(12) United States Patent
Bewley

(10) Patent No.: US 7,964,559 B2
(45) Date of Patent: Jun. 21, 2011

(54) MVL, AN ANTIVIRAL PROTEIN FROM A CYANOBACTERIUM

(75) Inventor: Carole A. Bewley, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1274 days.

(21) Appl. No.: 10/592,422

(22) PCT Filed: Mar. 9, 2005

(86) PCT No.: PCT/US2005/007703
§ 371 (c)(1),
(2), (4) Date: Sep. 11, 2006

(87) PCT Pub. No.: WO2005/087799
PCT Pub. Date: Sep. 22, 2005

(65) Prior Publication Data
US 2010/0029547 A1 Feb. 4, 2010

Related U.S. Application Data

(60) Provisional application No. 60/551,058, filed on Mar. 9, 2004.

(51) Int. Cl.
*A61K 38/16* (2006.01)
*B01J 20/26* (2006.01)
*C07K 14/195* (2006.01)

(52) U.S. Cl. ............ 514/3.7; 422/32; 502/7; 502/403; 514/3.8; 514/21.3; 530/324; 530/825

(58) Field of Classification Search .................. None
See application file for complete search history.

(56) References Cited

U.S. PATENT DOCUMENTS

| | | | |
|---|---|---|---|
| 4,870,015 A * | 9/1989 | Hoffman | 435/69.1 |
| 5,843,882 A | 12/1998 | Boyd | |
| 6,245,737 B1 | 6/2001 | Boyd et al. | |
| 6,420,336 B1 | 7/2002 | Boyd | |
| 6,428,790 B1 | 8/2002 | Boyd | |

FOREIGN PATENT DOCUMENTS

| WO | WO 00/70043 | 11/2000 |
|---|---|---|
| WO | WO 00/70043 A | 11/2000 |

OTHER PUBLICATIONS

Bewley et al. The Potent Anti-HIV Protein Cyanovirin-N . . . Journal of the American Chemical Society. 2001, vol. 123, No. 17, pp. 3892-3902.*
Kiessling et al. Strength in numbers: non-natural polyvalent carbohydrate derivatives. Chemistry & Biology. 1996, vol. 3, No. 2, pp. 71-77.*
Mammen et al. Polyvalent Interactions in Biological Systems . . . Angewandte Chemie International Edition. 1998, vol. 37, Issue 20, pp. 2754-2794.*
Yamaguchi M et al, "Isolation and characterization of a mannan-binding lectin from the freshwater cyanobacterium (blue-green algae) *Microcystis viridis*," Biochemical and Biophysical Research Communications, Nov. 30, 1999, pp. 703-708, vol. 265, No. 3.
International Search Report dated Sep. 7, 2005 issued in PCT/US2005/007703.
Yamaguchi et al., "*Isolation and Charaterization of a Mannan-Binding Lectin from the Freshwater Cyanobacterium (Blue-Green Algae) Microcystis viridis*", Biochemical and Biophysical Res. Comm., 265, pp. 703-708, 1999.
Tsai et al., "*Cyanovirin-N Gel as a Topical Microbicide Prevents Rectal Transmission of SHIV89.6P in Macaques*", AIDS Res. & Human Retroviruses, 19(7), pp. 535-542, 2003.
Kelley et al., "*Engineering an Obligate Domain-Swapped Dimer of Cyanovirin-N with Enhanced Anti-HIV Activity*", JACS, 124, pp. 3210-3211, 2002.

* cited by examiner

*Primary Examiner* — Jeffrey E Russel
(74) *Attorney, Agent, or Firm* — Edwards Angell Palmer & Dodge LLP; Peter F. Corless; Christine C. O'Day

(57) ABSTRACT

The present invention relates, e.g., to an isolated polypeptide from a cyanobacterium, *Microcystis viridis*, which binds specifically to an oligosaccharide comprising the tetrasaccharide Man-alpha-(1→6)Man-beta (1→4) GlcNAc-beta(1→4) GlcNAc. The polypeptide can be obtained, for example, from a cell that expresses a recombinant nucleic acid that encodes a MVL-like polypeptide. The invention also relates to an isolated polypeptide comprising one or more copies of the sequence GPLWSNXEAQXXGPX (SEQ ID NO: 1) and/or one or more copies of the sequence FTGQWXTX-VEXXMSV (SEQ ID NO: 2), wherein the polypeptide binds specifically to the above-mentioned oligosaccharide. Conjugates comprising such polypeptides and an effector molecule are also disclosed, as are methods of using such polypeptides or conjugates, e.g., for inhibiting infection by a virus, such as HIV, or for removing a virus, such as HIV, from a sample, such as a bodily fluid or an inanimate object.

26 Claims, 9 Drawing Sheets

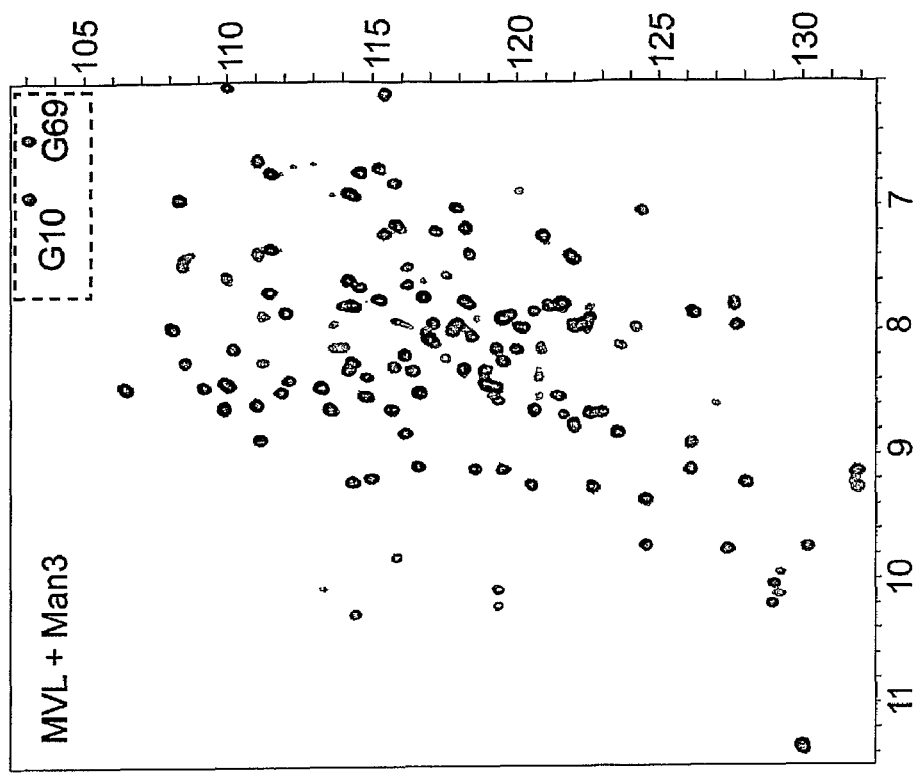
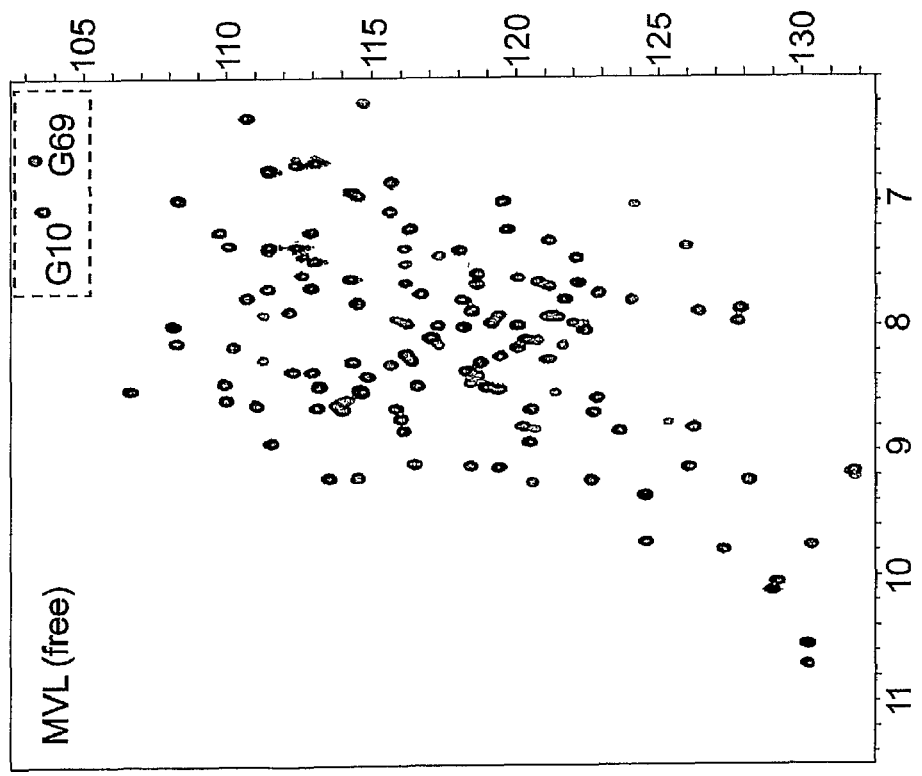
FIG. 3B
FIG. 3A

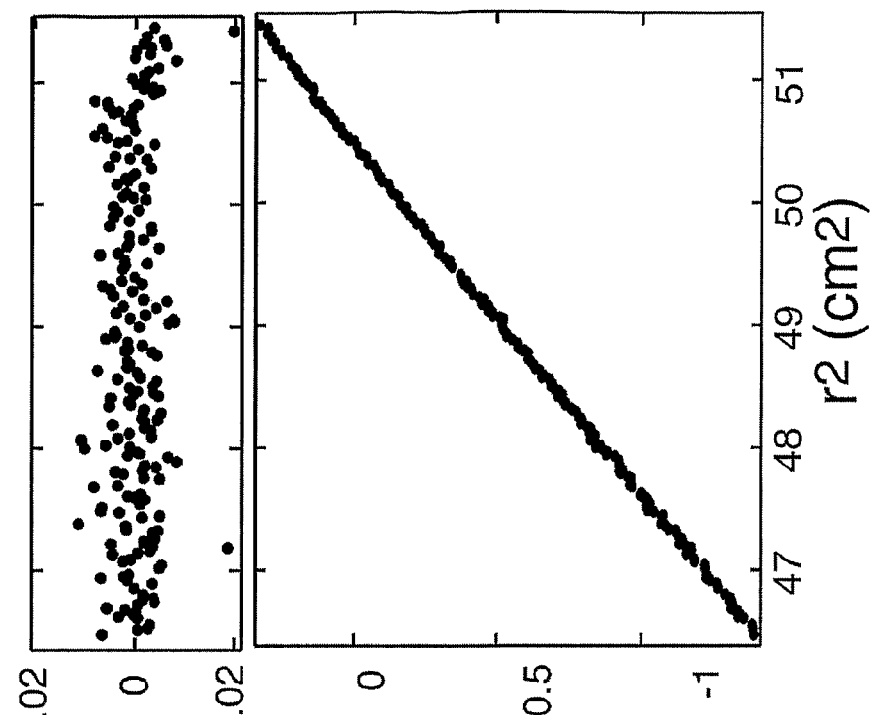
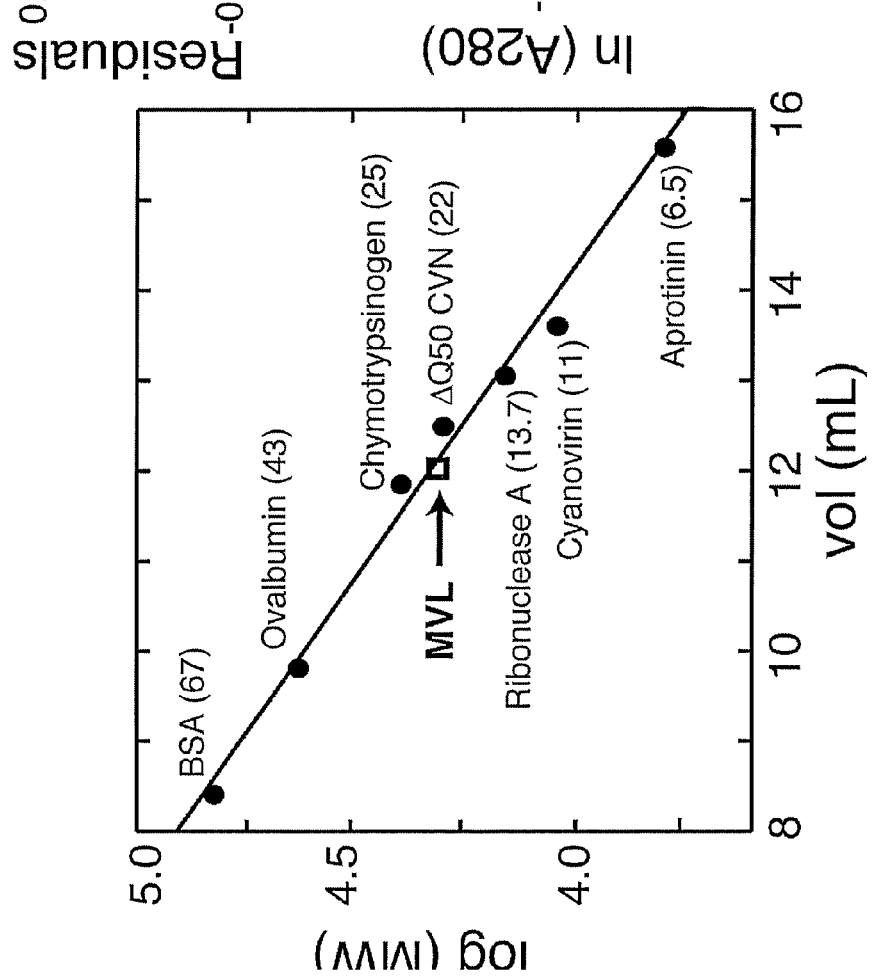
FIG. 5A
FIG. 5B

U.S. 7,964,559 B2

SEQUENCE LISTING

```
<160> NUMBER OF SEQ ID NOS: 8

<210> SEQ ID NO 1
<211> LENGTH: 15
<212> TYPE: PRT
<213> ORGANISM: Microcystis viridis
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 1

Gly Pro Leu Trp Ser Asn Xaa Glu Ala Gln Xaa Xaa Gly Pro Xaa
1               5                   10                  15

<210> SEQ ID NO 2
<211> LENGTH: 15
<212> TYPE: PRT
<213> ORGANISM: Microcystis viridis
<220> FEATURE:
<221> NAME/KEY: MOD_RES
```

```
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (11)..(12)
<223> OTHER INFORMATION: Any amino acid

<400> SEQUENCE: 2

Phe Thr Gly Gln Trp Xaa Thr Xaa Val Glu Xaa Xaa Met Ser Val
1               5                   10                  15

<210> SEQ ID NO 3
<211> LENGTH: 113
<212> TYPE: PRT
<213> ORGANISM: Microcystis viridis

<400> SEQUENCE: 3

Ala Ser Tyr Lys Val Asn Ile Pro Ala Gly Pro Leu Trp Ser Asn Ala
1               5                   10                  15

Glu Ala Gln Gln Val Gly Pro Lys Ile Ala Ala Ala His Gln Gly Asn
            20                  25                  30

Phe Thr Gly Gln Trp Thr Thr Val Val Glu Ser Ala Met Ser Val Val
        35                  40                  45

Glu Val Glu Leu Gln Val Glu Asn Thr Gly Ile His Glu Phe Lys Thr
    50                  55                  60

Asp Val Leu Ala Gly Pro Leu Trp Ser Asn Asp Glu Ala Gln Lys Leu
65                  70                  75                  80

Gly Pro Gln Ile Ala Ala Ser Tyr Gly Ala Glu Phe Thr Gly Gln Trp
                85                  90                  95

Arg Thr Ile Val Glu Gly Val Met Ser Val Ile Gln Ile Lys Tyr Thr
            100                 105                 110

Phe

<210> SEQ ID NO 4
<211> LENGTH: 578
<212> TYPE: DNA
<213> ORGANISM: Microcystis viridis
<220> FEATURE:
<221> NAME/KEY: CDS
<222> LOCATION: (142)..(483)

<400> SEQUENCE: 4
ggatccaaac caatcacttt taaccaaaag acaagacatt ttgcttaagg cattatggct      60
aactcaaaaa ttcagaaaag gatttttgat atcgtcttga ggatacaaaa tcaacaaaag     120
tctcaaagga cattatctat t atg gca agt tac aaa gtt aat atc cct gct      171
                        Met Ala Ser Tyr Lys Val Asn Ile Pro Ala
                        1               5                   10 ggg ccc ctc tgg agt aac gct gaa gca caa caa gta ggt ccg aaa att      219
Gly Pro Leu Trp Ser Asn Ala Glu Ala Gln Gln Val Gly Pro Lys Ile
                15                  20                  25 gca gct gcc cat caa gga aac ttt act ggt cag tgg aca acc gta gtt      267
Ala Ala Ala His Gln Gly Asn Phe Thr Gly Gln Trp Thr Thr Val Val
            30                  35                  40 gaa agt gca atg agt gta gta gaa gta gaa cta cag gtg gaa aat act      315
Glu Ser Ala Met Ser Val Val Glu Val Glu Leu Gln Val Glu Asn Thr
        45                  50                  55 gga att cat gaa ttt aaa act gat gtt tta gct gga cct ctc tgg agc      363
Gly Ile His Glu Phe Lys Thr Asp Val Leu Ala Gly Pro Leu Trp Ser
```

```
                   60                   65                  70
aac gat gaa gca caa aaa tta ggt ccg caa att gca gca tct tat ggt      411
Asn Asp Glu Ala Gln Lys Leu Gly Pro Gln Ile Ala Ala Ser Tyr Gly
 75                  80                  85                  90 gca gaa ttt act gga cag tgg cga acc att gtt gaa ggt gtc atg agt      459
Ala Glu Phe Thr Gly Gln Trp Arg Thr Ile Val Glu Gly Val Met Ser
                    95                 100                 105 gtt att caa atc aag tac act ttc taagtgcgat cgcctctctt atcggttaga     513
Val Ile Gln Ile Lys Tyr Thr Phe
                110 ttgaggtacg gaacccaaca ctatttaagg tgtgttactt cggtgatgca cctttactg     573 gatcc                                                                578

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggtgcgagc atatggcgag ttacaaagtg                                      30

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggccacgctc gagttagaaa gtgtacttg                                       29

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 114
<212> TYPE: PRT
<213> ORGANISM: Microcystis viridis

<400> SEQUENCE: 8

Met Ala Ser Tyr Lys Val Asn Ile Pro Ala Gly Pro Leu Trp Ser Asn
1               5                   10                  15

Ala Glu Ala Gln Gln Val Gly Pro Lys Ile Ala Ala His Gln Gly
                20                  25                  30

Asn Phe Thr Gly Gln Trp Thr Thr Val Val Glu Ser Ala Met Ser Val
            35                  40                  45

Val Glu Val Glu Leu Gln Val Glu Asn Thr Gly Ile His Glu Phe Lys
        50                  55                  60

Thr Asp Val Leu Ala Gly Pro Leu Trp Ser Asn Asp Glu Ala Gln Lys
65                  70                  75                  80
```

-continued

```
Leu Gly Pro Gln Ile Ala Ala Ser Tyr Gly Ala Glu Phe Thr Gly Gln
                85                  90                  95

Trp Arg Thr Ile Val Glu Gly Val Met Ser Val Ile Gln Ile Lys Tyr
            100                 105                 110

Thr Phe
```

MVL, AN ANTIVIRAL PROTEIN FROM A CYANOBACTERIUM

This application claims the benefit of the filing date of U.S. provisional application 60/551,058, filed Mar. 9, 2004, which is incorporated by reference herein in its entirety.

FIELD OF THE INVENTION

This invention relates generally to proteinaceous agents that bind specifically to defined oligosaccharides found, for example, in the envelopes of certain viruses, including HIV. Methods are described that use the proteinaceous agents, for example methods for inhibiting infection by viruses, including HIV.

BACKGROUND INFORMATION

Acquired immune deficiency syndrome (AIDS) is a fatal disease. More than 40 million people in the world today are infected with the AIDS virus. The AIDS virus was first identified in 1983, and it has been known by several names and acronyms, including lymphadenopathy-associated virus (LAV), AIDS-related virus (ARV), T-lymphotropic virus III (HTLV-III), and human immunodeficiency virus (HIV). Two distinct families of HIV have been described to date, HIV-1 and HIV-2. The acronym HIV is used herein to refer to human immunodeficiency viruses generically. The AIDS virus is a retrovirus, a virus that uses reverse transcriptase during replication; it has the capacity to replicate within cells of the immune system, causing profound cell destruction.

Current therapeutic regimens have focused on reverse transcriptase and protease inhibitors, but the emergence of mutant drug resistance strains has created a need for more effective and less toxic anti-HIV agents.

Human and related primate immunodeficiency viruses enter a target cell by way of an orchestrated series of recognition events between the invading virus and the target host cell. These include, e.g., interaction of the viral envelope glycoprotein (generically termed "gp120" herein) with the cell surface receptor CD4, followed by subsequent interactions between gp120 and a target cell co-receptor (such as the chemokine receptors, CXCR4, CCR5, etc). The conformational changes brought about by this multi-protein assembly facilitate membrane fusion (e.g., mediated by the "stalk" protein of the viral receptor, the gp41 protein), which is followed by virus entry. Productively infected, virus-producing cells express gp120 at the cell surface; and interaction of gp120 of infected cells with CD4 on uninfected cells results in formation of dysfunctional multicellular syncytia and further spread of viral infection. Thus, interactions between viral envelope proteins, such as gp120, and proteins such as cell surface receptor molecules, e.g., CD4, CXCR4 or CCR5, are particularly attractive targets for interruption of HIV infection and cytopathogenesis, either by prevention of initial virus-to-cell binding or by blockage of cell-to-cell fusion. Virus-free or "soluble" gp120 shed from virus or from infected cells in vivo is also an important therapeutic target, since it may otherwise contribute to noninfectious immunopathogenic processes throughout the body, including the central nervous system.

Several agents have been described that that can block viral envelope (Env)-mediated fusion. One class of such agents is composed of peptides and proteins, including engineered envelope or receptor-derived peptides and proteins. Depending on their size and stability, such inhibitors have the potential to be used as antivirals in vivo or ex vivo. Examples of engineered proteins and peptides that inhibit viral entry include those that target the pre-fusogenic form of gp41 and those that target receptor binding sites on gp120. Examples of nanomolar gp41 inhibitors include the peptides Fuzeon™ (Wild et al. (1994) *Proc. Natl. Acad. Sci. U.S.A.* 91, 9770-9774), C34 (Chan et al. (1998) *Proc. Natl. Acad. Sci. U.S.A.* 95, 15613-15617) and N36[Mut]e,g (Bewley et al. (2002) *J. Biol. Chem.* 277, 14238-14245), and the engineered proteins $N_{CCG}$-gp41 (Louis et al. (2001) *J. Biol. Chem.* 276, 29485-29489), $N35_{CCG}$-N13 (Louis et al. (2003) *J. Biol. Chem.* 278, 20278-20285) and 5-helix (Root et al. (2001) *Science* 291, 884-888). Examples of natural proteins that inhibit HIV-1 envelope mediated fusion include cyanovirin-N (CVN) (Boyd et al. (1997) *Antimicrob. Agents. Chemother.* 41, 1521-1530), scytovirin (Bokesch et al. (2003) *Biochemistry* 11, 2578-2584), and actinohivin (Chiba et al. (2001) *Biochem. Biophys. Res. Commun.* 30, 595-601). Interestingly, the three preceding proteins were all isolated from prokaryotic organisms, with CVN and scytovirin coming from the cyanobacteria *Nostoc ellipsosporum* and *Scytonema varium*, respectively, and actinohivin from an actinomycete strain.

*Microcystis viridis* NIES-102 is a freshwater bloom-forming cyanobacterium that was observed to have transient hemagglutinating activity when grown under anaerobic conditions in the laboratory. This activity was traced to a 113 amino acid, 13 kDa protein, termed MVL, the gene for which was cloned and sequenced (Yamaguchi et al. (1999) *Biochem. Biophys. Res. Commun* 265, 703-708). The present patent describes variants of that protein, and methods for using the protein and the variants, e.g., methods for inhibiting infection by viruses, including HIV.

The middle panel shows the first portion of SEQ ID NO: 3; the bottom panel shows the remainder of the sequence. Carbohydrate binding regions were delineated by $\Delta\delta_{SUM}$ values where $\Delta\delta_{SUM}=\sqrt{(\Delta\delta_{HN}^2+\Delta\delta_{N}^2)}$, and $\Delta\delta_{HN}$ and $\Delta\delta_{N}$ are the differences in Hz between pairs of free and bound HN and N resonances, respectively. Note that $\Delta\delta$ values for HN and/or N atoms could not be determined for Asn15, Gly35, Glu42, Asn74, and Gly94 due to overlap. Amino acid sequence and numbering appear along the x axis where the tandem repeats are aligned by internal sequence homology. The identical and conserved residues within the two tandem repeats are indicated in the top panel.

Figure 3C:
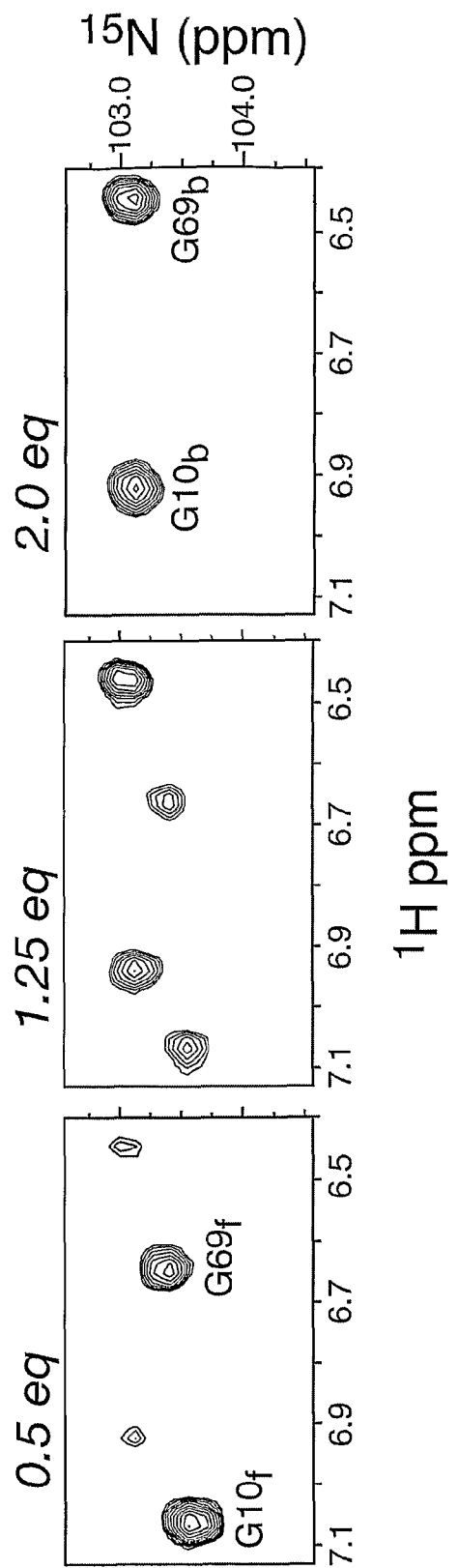

FIGS. 3A-3C show $^1$H—$^{15}$N correlation spectra for complexes of free and oligomannose-bound MVL. FIG. 3A shows the spectrum for free MVL. FIG. 3B shows the spectrum for a complex of 1:4 MVL:Man3GlcNAc2. FIG. 3C shows an expansion of the $^1$H, $^{15}$N correlation spectra for individual points in the Man3 titration which ranged from 0.25 to 2.0 equivalents oligosaccharide. Based on the concentration of monomeric MVL determined by UV absorbance ($\epsilon$=26,600 M-1 cm-1 for monomer), the integrated volume of cross peaks appearing upon addition of Man3GlcNAc2 where oligosaccharide is added 0.25 equivalents at a time were approximately half that expected for full occupancy of one site.

Figure 4B:
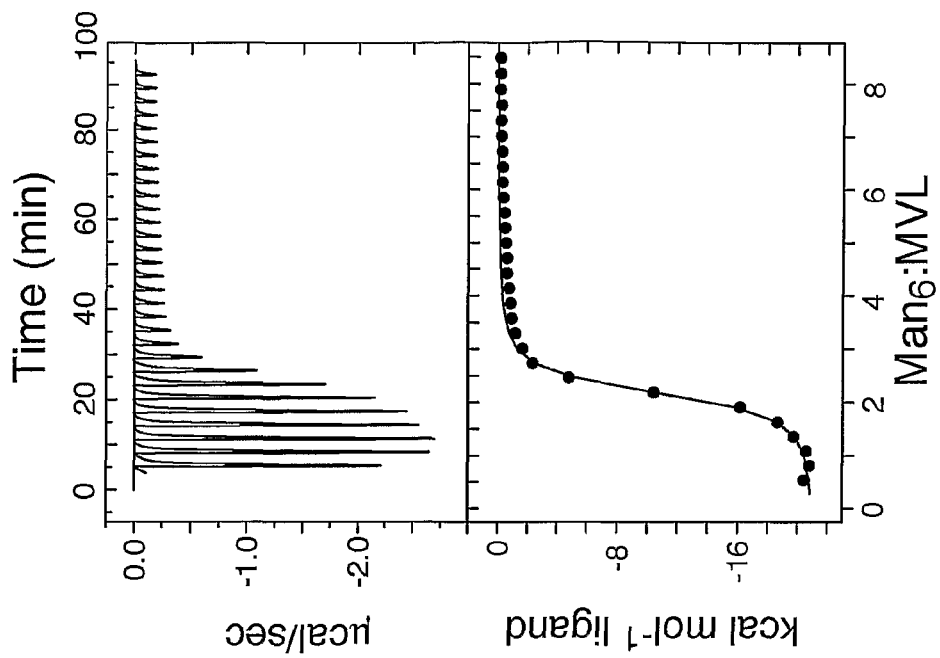
Figure 4A:
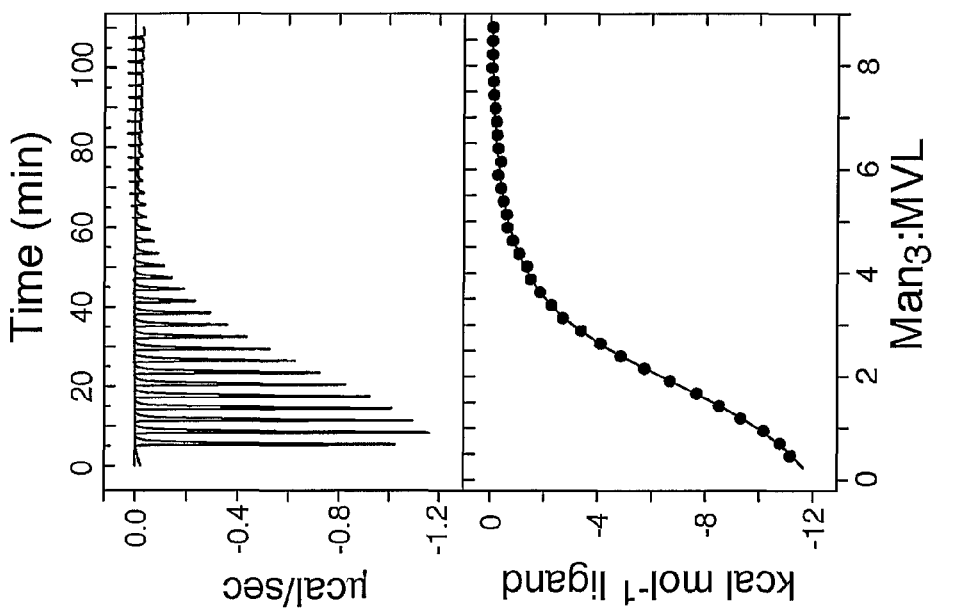

FIGS. 4A and 4B show ITC of binding of $Man_3GlcNAc_2$ and $Man_6GlcNAc_2$ to MVL. Raw data as a function of time for the two oligomannosides are shown in the upper panel of FIGS. 4A and 4B, respectively; and plots of the total heat released as a function of the molar ratio of each ligand are shown in the respective lower portions of the figures. The continuous lines represent the non-linear least-squares best fits to the experimental data using a one site model. The values of the fitted parameters $K_A$ and $\Delta H$ are provided in Table 2.

Figure 5C:
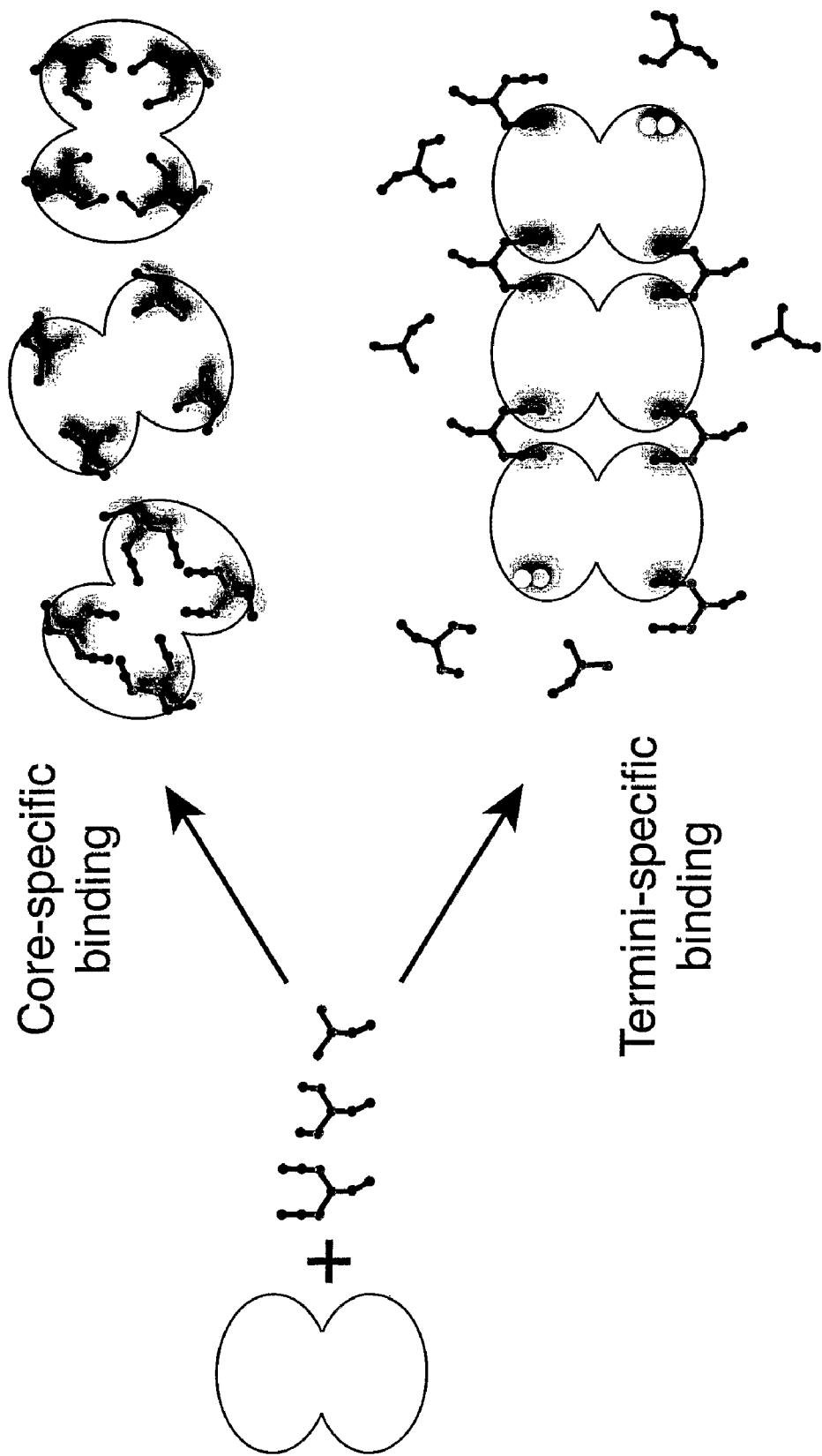

FIGS. 5A-5C show the oligomeric nature of, and a model of, carbohydrate binding of MVL. The molecular mass of MVL was determined by gel filtration chromatography (FIG. 5A) and sedimentation equilibrium experiments (FIG. 5B). In FIG. 5A, a plot of log [molecular weight] as a function of elution volume for the proteins indicated shows a linear relationship between the two giving an estimated molecular mass for MVL of 25.4 kDa. FIG. 5B shows sedimentation equilibrium profile at 16,000 rpm and 25° C. shown as a distribution of ln ($A_{280}$) at equilibrium. The results are analyzed for the best single component M(1-vρ) fit, corresponding to a measured molecular mass of 23,340±400 g mol$^{-1}$. The distribution of the residuals to the best single component fit is shown above the plot. FIG. 5C shows a model of multi-domain binding to oligosaccharides. The top part of the figure illustrates specificity for core or non-branching structures wherein each carbohydrate binding site is saturated but not cross-linked since the non-branching structures do not facilitate cross-linking; while the bottom part of the figure illustrates specificity for saccharides located at the termini of the arms of branched oligosaccharides and are thus capable of inducing cross-linking.

Figure 6A:
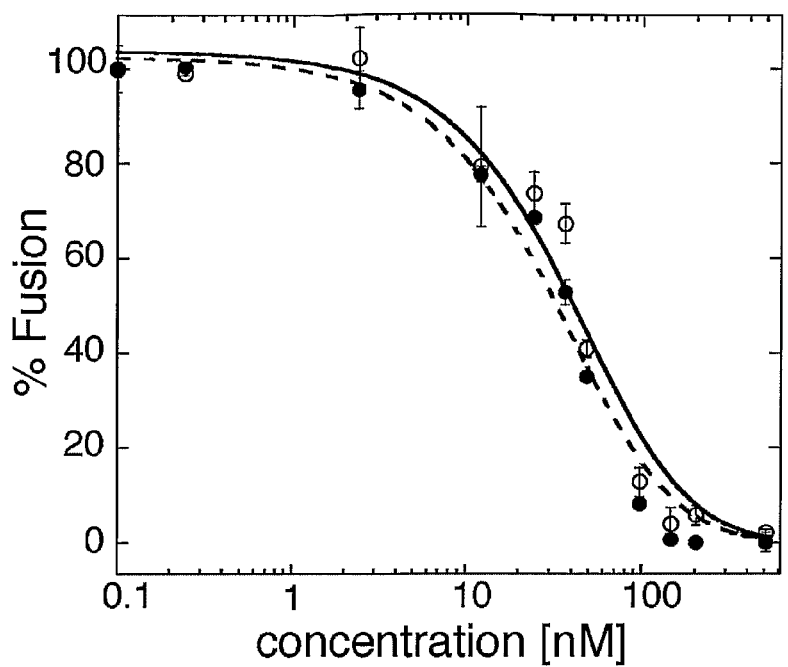
Figure 6B:
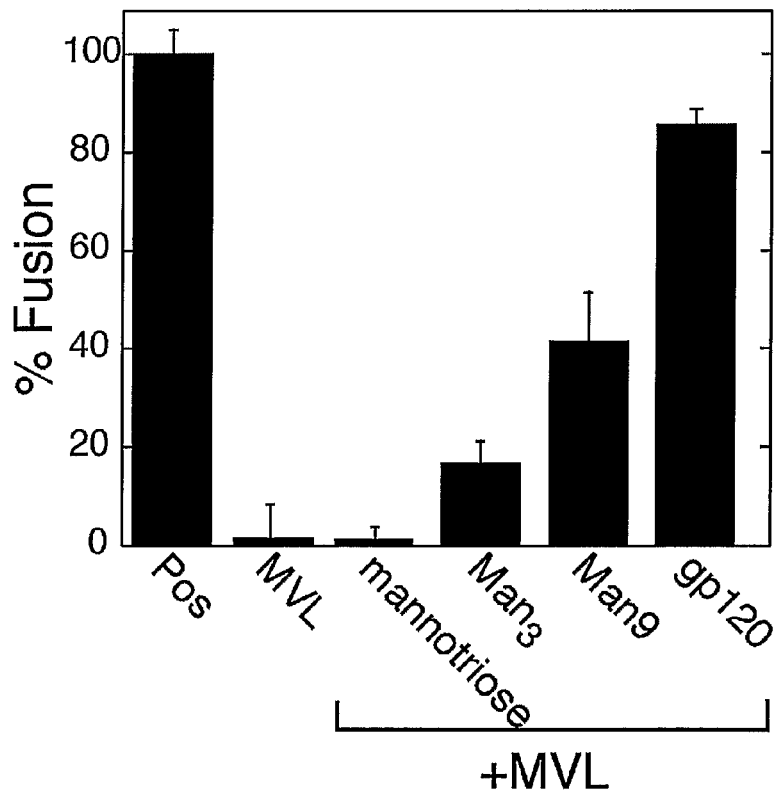

FIGS. 6A-6B show HIV-1 Env-mediated cell fusion by MVL and complexes. In FIG. 6A, the effect of MVL on fusion is indicated with solid circles for T-tropic virus (LAV) and with open circles for M-tropic virus (SF162); error bars are indicated. A solid line (M-tropic) and a dotted line (T-tropic) represent best fits to the data using the activity relationship of a two-independent site model: % fusion=100/ $(1+2K_A[I]+K_A^2[I]^2)$ where [I] is the concentration of MVL and $K_A$ is the equilibrium association constant for MVL binding to trimeric gp120. (Best fits yield $IC_{50}$ values, given by $(\sqrt{2}-1)/K_A$, of 30±4 nM for LAV and 37±6 nm for SF162. FIG. 6B shows the effect on fusion-blocking activity of MVL (200 nM) upon pretreatment with a 5-fold excess of mannotriose, $Man_3GlcNAc_2$ or $Man_9GlcNAc_2$, and one equivalent of gp120 (SF162). Negative and positive controls were performed for all experiments and were used for normalization. Controls for each of the ligands in the absence of MVL were also carried out and yielded results indistinguishable from those of the positive controls, that is, they had no effect on % fusion.

Figure 7A:
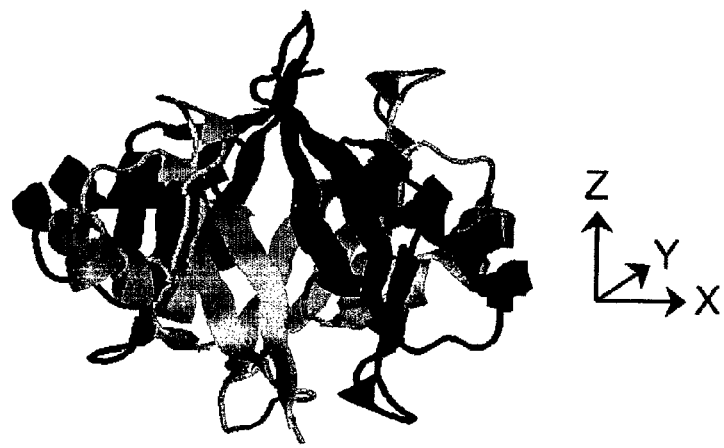
Figure 7B:
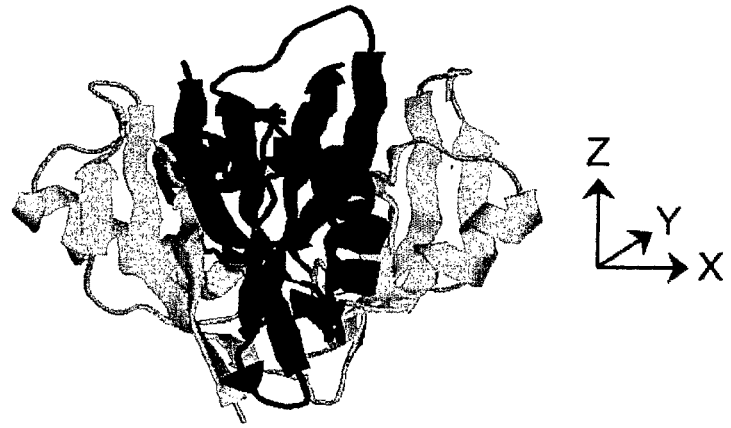
Figure 7C:

FIGS. 7A-7C show ribbon diagrams of MVL, as determined by NMR and X-ray crystallography. In FIG. 7A, the structure shown in FIG. 7B has been rotated approximately 100 degrees about the Z-axis. In FIG. 7C, the structure has been rotated 90 degrees about the X-axis relative to the structure in FIG. 7A. The two molecules of MVL present in the dimeric form are black and grey. The locations of the four carbohydrate binding sites are shown with arrows in FIG. 7C, which also delineate the four homologous domains of the protein.

DESCRIPTION OF THE INVENTION

The inventor reports herein that the carbohydrate binding protein (lectin), MVL, binds specifically to oligosaccharides comprising the tetrasaccharide, Manα(1→6)Manβ(1→4) GlcNAcβ(1→4)GlcNAc, and that it binds to such oligosaccharides with unexpectedly high (nanomolar) affinity. This lectin is also shown, unexpectedly, to inhibit envelope-mediated fusion of viruses, including HIV-1, to their target cells, thereby potently inhibiting viral infection. The inhibition of HIV-1 fusion is shown to be mediated, at least in part, by binding of the lectin to carbohydrate residues of the glycoprotein, gp120, an envelope protein of the virus. The results presented herein characterize the structure of the lectin by several criteria, and delineate portions of the protein which are involved in the carbohydrate binding; this characterization facilitates the design of fragments and variants of the lectin that retain, e.g., the high affinity and specificity of the wild type MVL protein.

This invention relates, e.g., to MVL-related polypeptides, including active fragments and variants of the wild type protein, conjugates comprising those polypeptides, and pharmaceutical compositions comprising the polypeptides or conjugates; nucleic acids encoding those polypeptides or conjugates; therapeutic and prophylactic antiviral methods employing the polypeptides, conjugates or pharmaceutical compositions; and methods using compositions of the invention for removing viruses, such as HIV, from liquids, including blood or blood products, or from inanimate objects, including medical devices.

Polypeptides of the invention can also be used for experimental purposes. For example, complexes formed between the polypeptides and their carbohydrate ligands represent novel templates for protein-carbohydrate recognition, and can be used to increase the understanding of the interactions required to achieve high affinity protein-carbohydrate binding.

Advantages imparted by the high degree of specificity and affinity of polypeptides of the invention for the mentioned class of oligosaccharides include the ability of the polypeptides to function effectively as specific virucidal agents, in vivo or ex vivo (e.g., following topical administration of the lectin) or as agents for removing unwanted virus from substances such as blood products or medical equipment. Polypeptides of the invention act early in the viral cycle, e.g., to inhibit entry of a virus into a target cell, and thus can function potentially at a variety of steps during the infection process, e.g. to inhibit initial infection of target cells; to inhibit infection of newly produced, uninfected immune cells generated in the body in response to the virus-induced killing of infected cells; to block cell-to-cell fusion; to neutralize or inhibit new infectious virus produced by infected cells; and/or to target virus-free or "soluble" gp120 shed from virus or from infected cells, thereby inhibiting noninfectious immunopathogenic processes throughout the body, including the central nervous system. Another advantage of the polypeptides of the invention is that they are not hampered by hyper-variability of the gp120-neutralizing determinants, which contributes to the extreme strain-dependence of viral sensitivity to gp120-directed antibodies, another type of antiviral agent that is currently under investigation. Further advantages of the polypeptides of the invention are that they are relatively non-toxic to host cells; are resistant to degradation under physiological and rigorous environmental conditions; and are readily and inexpensively produced on a large-scale basis.

Figure 1:
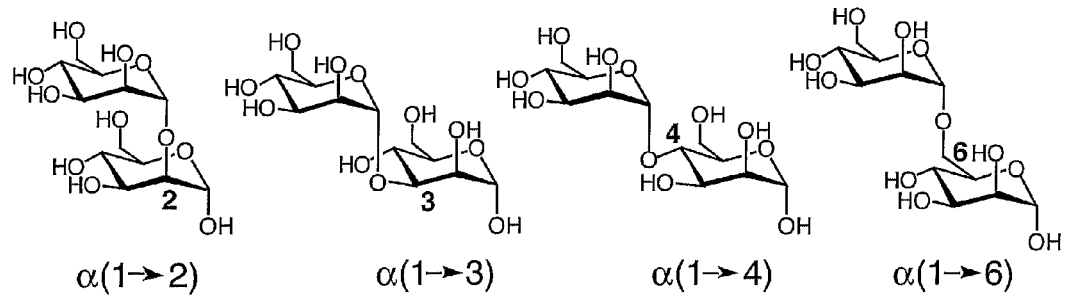
FIG. 1 shows some of the carbohydrates used for NMR titrations. Both alpha-and beta-linked di-mannosides were used for titrations, but only alpha-linked structures are shown. Manα(1→4)GlcNAc and GlcNAcβ(1→4)GlcNAc ("GlcNAc$_2$") are disaccharides corresponding to the core, and "mannotriose" refers to the trisaccharide Manα (1→3)[Manα(1→6)]Manβ. Man$_2$A refers to the tetrasaccharide Manα(1→6)Manβ(1→4)GlcNAcβ(1→4)GlcNAc. Structures corresponding to Man$_3$GlcNAc$_2$ (Man$_3$), Man$_6$GlcNAc$_2$ (Man$_6$), and Man$_9$GlcNAc$_2$ (Man$_9$) are indicated respectively with arrows within the Man$_9$GlcNAc$_2$ structure, and standard designations for each pyranose are indicated in bold italics.
Figure 1:
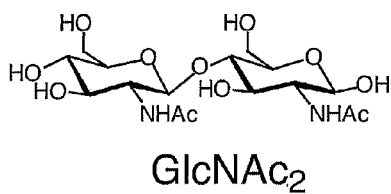
Figure 1:
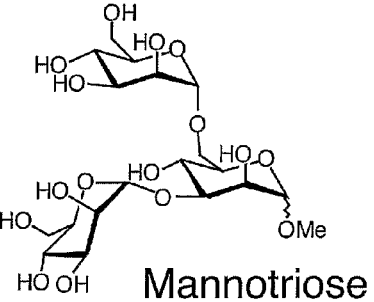
Figure 1:
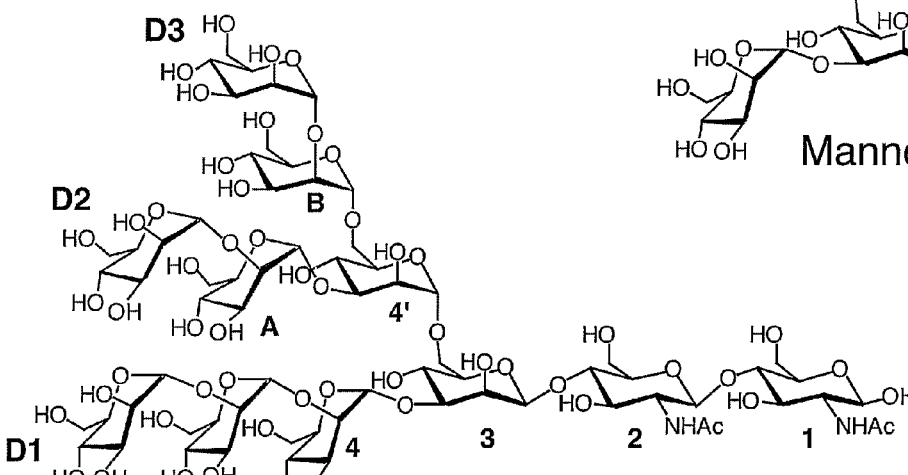
Figure 1:
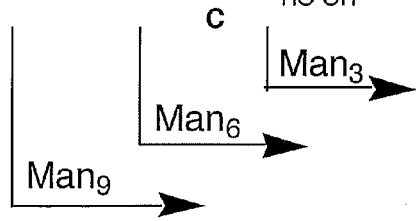
Figure 1:

The present invention relates, e.g., to an isolated MVL-like polypeptide expressed by the cyanobacterium *Microcystis viridis* (preferably the strain *Microcystis viridis* NIES-102), which binds specifically to an oligosaccharide (e.g., a high mannose oligosaccharide) comprising the tetrasaccharide Man-alpha-(1→6)Man-beta (1→4) GlcNAc-beta(1→4) GlcNAc. The polypeptide can be obtained from a naturally occurring *Microcystis viridis* bacterium; or it can be obtained from a cell (e.g., a bacterium) that expresses the polypeptide recombinantly (e.g., a cell that has been transfected with a nucleic acid comprising a sequence encoding MVL (e.g., SEQ ID NO: 4), operably linked to an expression control sequence). Polypeptides referred to herein as MVL polypeptides "from the cyanobacterium *Microcystis viridis* (preferably the strain *Microcystis viridis* NIES-102)" include both polypeptides isolated from the naturally occurring bacterium, and polypeptides obtained recombinantly as described above. This tetrasaccharide is illustrated in FIG. 1, where it is referred to as Man$_2$-A. In some embodiments, the polypeptide does not comprise SEQ ID NO: 3 (the full-length sequence of wild type MVL, as reported disclosed by Yamaguchi et al., 1999, supra).

The term "isolated," when referring, e.g. to a polypeptide or polynucleotide, means that the material is removed from its original environment (e.g., the natural environment if it is naturally occurring), and isolated or separated from at least one other component with which it is naturally associated. For example, a naturally-occurring polypeptide present in its natural living host is not isolated, but the same polypeptide, separated from some or all of the coexisting materials in the natural system, is isolated. Such polypeptides could be part of a composition, and still be isolated in that such composition is not part of its natural environment. The term "an isolated polypeptide," as used herein, can include 1, 2, 3, 4 or more copies of the polypeptide, i.e., the polypeptide can be in the form of a monomer, or it can be in the form of a multimer, such as dimer, trimer, tetramer or the like.

By a polypeptide binding "specifically" to a particular oligosaccharide is meant that the polypeptide binds selectively (preferentially) to that oligosaccharide, or to a polysaccharide or glycoprotein comprising the oligosaccharide, in comparison to other oligosaccharides.

Full length, wild type MVL was reported by Yamaguchi et al., 1999, supra to have the following sequence:

```
                                          (SEQ ID NO: 8)
GGA TCC AAA CCA ATC ACT TTT AAC CAA AAG ACA AGA

CAT TTT GCT TAA GGC ATT ATG GCT AAC TCA AAA ATT

CAG AAA AGG ATT TTT GAT ATC GTC TTG AGG ATA CAA

AAT CAA CAA AAG TCT CAA AGG ACA TTA TCT ATT ATG
                    SD                       (M)
```

```
                              -continued
GCA AGT TAC AAA GTT AAT ATC CCT GCT GGG CCC CTC
 A   S   Y   K   V   N   I   P   A   G   P   L TGG AGT AAC GCT GAA GCA CAA CAA GTA GGT CCG AAA
 W   S   N   A   E   A   Q   Q   V   G   P   K ATT GCA GCT GCC CAT CAA GGA AAC TTT ACT GGT CAG
 I   A   A   A   H   Q   G   N   F   T   G   Q TGG ACA ACC GTA GTT GAA AGT GCA ATG AGT GTA GTA
 W   T   T   V   V   E   S   A   M   S   V   V GAA GTA GAA CTA CAG GTG GAA AAT ACT GGA ATT CAT
 E   V   E   L   Q   V   E   N   T   G   I   H GAA TTT AAA ACT GAT GTT TTA GCT GGA CCT CTC TGG
 E   F   K   T   D   V   L   A   G   P   L   W AGC AAC GAT GAA GCA CAA AAA TTA GGT CCG CAA ATT
 S   N   D   E   A   Q   K   L   G   P   Q   I GCA GCA TCT TAT GGT GCA GAA TTT ACT GGA CAG TGG
 A   A   S   Y   G   A   E   F   T   G   Q   W GGA ACC ATT GTT GAA GGT GTC ATG AGT GTT ATT CAA
 R   T   I   V   E   G   V   M   S   V   I   Q

ATG AAG TAC ACT TTC TAA GTG CGA TCG CCT CTC TTA
 I   K   Y   T   F   *

TCG GTT AGA TTG AGG TAC GGA AGC CAA CAC TAT TTA (SEQ ID NO: 4)
AGG TGT GTT ACT TCG GTG ATG CAC CTT TTA CTG GAT CC
```

Figure 2:
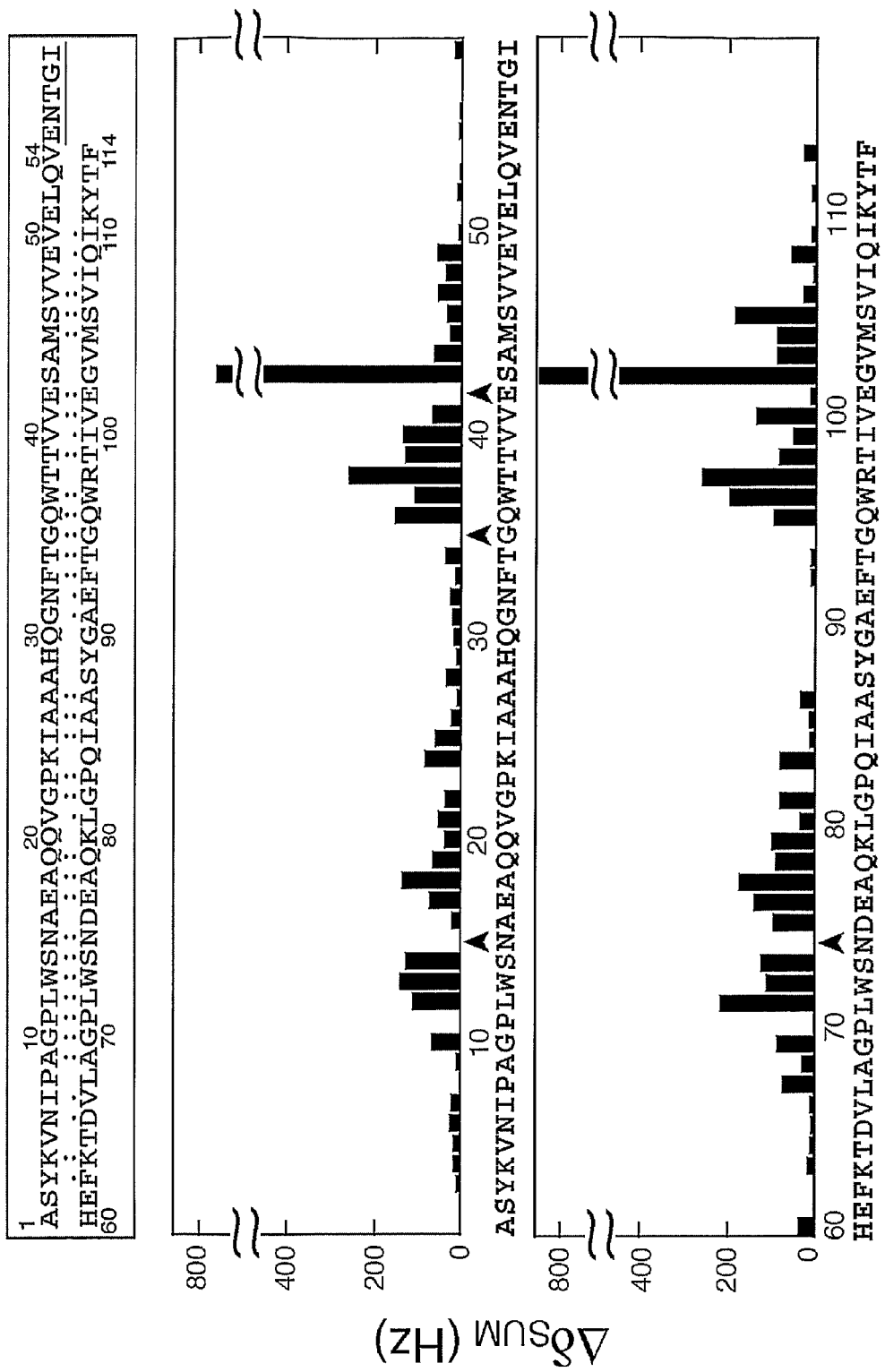
FIG. 2 shows the amino acid residues involved in carbohydrate binding, as determined by nuclear magnetic resonance (NMR) spectroscopy. MVL comprises an N-and C-terminal region with 50% identity between the two 54 amino acid repeats that are connected by a sequence of five amino acids. The upper panel of the figure shows an alignment of the first portion (amino acid residues 1-59, from the N-terminal portion of the MVL protein) of SEQ ID NO: 3 compared to the second portion of the sequence (amino acid residues 60-114, from the C-terminal portion of the protein). Double dots indicate identical residues; single dots indicate conserved amino acids.

As noted, the amino acid sequence is represented by SEQ ID NO:8. This is identical to SEQ ID NO:3, as shown in FIG. 2, except that SEQ ID NO:8 shows (in parentheses) the N-terminal Met which is removed during processing of the protein. "Full-length" MVL has the sequence represented by SEQ ID NO: 3. The numbering of amino acids in this patent application corresponds to the sequence of SEQ ID NO: 3. SEQ ID NO:4 is a nucleic acid sequence that comprises a sequence which encodes the amino acids of SEQ ID NO:8.

The MVL-like polypeptides of the invention, which bind specifically to an oligosaccharide (e.g., a high mannose oligosaccharide) comprising the tetrasaccharide Man-alpha-(1→6)Man-beta(1→4)GlcNAc-beta(1→4)GlcNAc, include active fragments and variants of the wild type polypeptide. For example, they include allelic variants or naturally occurring mutations of the wild type protein. Other types of variants, as discussed elsewhere herein, are also included.

Another aspect of the invention is an isolated polypeptide comprising one or more copies of the sequence GPLWSNX-EAQXXGPX (SEQ ID NO: 1) and/or one or more copies of the sequence FTGQWXTXVEXXMSV (SEQ ID NO: 2), and/or comprising one or more copies of an active variant of SEQ ID NO: 1 and/or SEQ ID NO: 2; wherein the polypeptide binds specifically to an oligosaccharide (e.g., a high mannose oligosaccharide) comprising the tetrasaccharide Man-alpha-(1→6)Man-beta(1→4)GlcNAc-beta(1→4)GlcNAc. In some embodiments, the polypeptide does not comprise SEQ ID NO: 3.

Any of the polypeptides of the invention, such as those described above, may be in the form of a monomer, or in the form of a multimer, such as dimer, trimer, tetramer or the like. The different types of polypeptides may be homo-multimers, or the different types may be mixed and matched to form hetero-multimers. Preferably, the polypeptide is a homodimer.

In particularly preferred embodiments, a polypeptide of the invention may comprise one or more copies of SEQ ID NO:1 and/or one or more copies of SEQ ID NO: 2; or it may comprise one or more copies of SEQ ID NO: 1 and one or more copies of SEQ ID NO: 2; or it may comprise two copies of SEQ ID NO: 1, which are located approximately at positions 10-24 and 69-83 of the polypeptide, and two copies of SEQ ID NO: 2, which are located approximately at positions 33-47 and 92-106 of the polypeptide.

A polypeptide of the invention generally binds specifically to an oligosaccharide (e.g., a high mannose oligosaccharide) comprising the tetrasaccharide Man-alpha-(1→6)Man-beta (1→4) GlcNAc-beta(1→4)GlcNAc ($Man_2$-A). The oligosaccharide may be free in solution, or it may form part of a glycoprotein. As used herein, the term "oligosaccharide" refers to a carbohydrate molecule having a molecular weight less than about 10,000; and a "polysaccharide" refers to a carbohydrate molecule having a molecular weight greater than about 10,000. In general, carbohydrates on viral envelope proteins are oligosaccharides, rather than polysaccharides. In one embodiment, a polypeptide of the invention inhibits fusion of an organism comprising, on its surface, $Man_2$-A to a target cell. The organism, may be, e.g., a bacterium or a parasite. Preferably, a polypeptide of the invention exhibits antiviral activity. In embodiments of the invention, the polypeptide inhibits fusion of an enveloped virus comprising a glycoprotein comprising $Man_2$-A to a target cell. In a preferred embodiment, the virus is a retrovirus, such as a lentivirus, e.g., a human immunodeficiency virus, such as HIV-1 or HIV-2.

Another aspect of the invention is a conjugate of a polypeptide of the invention and an effector molecule. The effector molecule can be, e.g., an agent that enhances the antiviral activity of the polypeptide, an agent that stabilizes or otherwise enhances the efficiency of the polypeptide, or an immunological agent. In embodiments of the invention, the effector molecule is, e.g., a toxin (such as a *Pseudomonas* exotoxin or a ricin component), another antiviral agent, or polyethylene glycol, albumin or dextran.

As used herein, the singular forms "a," "an," and "the" include plural referents unless the context clearly dictates otherwise. For example, "an" effector molecule, as used above, means one or more effector molecules, which can be the same or different.

Another aspect of the invention is a pharmaceutical composition comprising a polypeptide or conjugate of the invention and a pharmaceutically acceptable carrier. Preferably, a polypeptide or conjugate in the composition is in an amount which is effective for inhibiting infection by a virus, or by another organism as discussed herein. In a preferred embodiment, the pharmaceutical composition is formulated for topical administration.

Another aspect of the invention is a method for treating an inanimate object, comprising contacting it with a polypeptide or conjugate of the invention. Preferably, the polypeptide or conjugate acts as an antiviral agent, and it is in an antiviral effective amount. The term an "antiviral effective" amount, as used herein, is an amount that can inhibit a viral infection, at least to a measurable degree. Suitable inanimate objects include, e.g., medical equipment, medical supplies (such as medical tubing), laboratory equipment and laboratory supplies.

Another aspect of the invention is a method for treating a solution, suspension, emulsion or other material by contacting it with a polypeptide or conjugate of the invention. Preferably, the polypeptide or conjugate acts as an antiviral agent, and it is in an antiviral effective amount.

Another aspect of the invention is a method for treating ex vivo a bodily product or tissue with a polypeptide or conjugate of the invention. Preferably, the polypeptide or conjugate acts as an antiviral agent, and it is in an antiviral effective amount. In some embodiments, the polypeptide or conjugate is in the form of a pharmaceutical composition. Suitable bodily products include, e.g., blood, a product of blood, or sperm. In embodiments of this method, the polypeptide or conjugate (e.g., in the form of a pharmaceutical composition) is on or in medical equipment, medical supplies, laboratory equipment, laboratory supplies, or any solution, suspension, emulsion or other material; for example, it may be on the wall of a medical tubing. In embodiments of this method, one or more of the polypeptides or conjugates are attached to or part of a solid support matrix; or one or more of the polypeptides or conjugates bind to gp120 of HIV.

Another aspect of the invention is a method for removing a virus from a sample, comprising contacting a sample suspected of containing the virus with a composition comprising a polypeptide or conjugate of the invention, preferably wherein the polypeptide and/or conjugate is attached to a solid support matrix, under conditions effective for binding of the virus in the sample to the polypeptide and/or conjugate; and separating the sample and the composition, whereupon virus is removed from the sample. In a preferred embodiment, the support matrix comprises magnetic beads and the sample and the composition are separated by contact with a magnet. In embodiments of this method, the sample is blood, a component of blood, sperm, cells, tissue or an organ; and/or the virus that is removed is HIV.

Another aspect of the invention is a method for isolating an oligosaccharide or polysaccharide comprising Man-alpha-(1→6)Man-beta (1→4) GlcNAc-beta(1→4)GlcNAc, comprising contacting a sample suspected of comprising said oligosaccharide or polysaccharide with a composition comprising a polypeptide or conjugate of the invention, preferably wherein the polypeptide and/or conjugate is attached to a solid support matrix, under conditions effective for binding of the oligosaccharide or polysaccharide in the sample to the isolated polypeptide and/or conjugate in the composition; and separating the sample and the composition, whereupon said oligosaccharide or polysaccharide is removed from other components of the sample.

Another aspect of the invention is a composition comprising a solid matrix to which is attached a virus-binding effective amount of a polypeptide or conjugate of the invention. In embodiments of this composition, the solid support matrix comprises magnetic beads or a flow-through matrix; or the solid support matrix comprises a condom, a diaphragm, a cervical cap, a vaginal ring, a dental dam, or a sponge.

Another aspect of the invention is a method for inhibiting an infection of a host, such as a viral infection, comprising administering to the host an effective amount of a formulation comprising a polypeptide or conjugate of the invention. The inhibition may be prophylactic or therapeutic. The inhibition may be of infectivity and/or a cytopathic effect of a viral infection. In a preferred embodiment, the virus is an enveloped virus, e.g., a retrovirus, such as a lentivirus, in particular, a human immunodeficiency virus, such as HIV (e.g., HIV-1 or HIV-2). In a preferred embodiment, the formulation is administered topically, e.g., to the vagina, penis, rectum or mouth of the host. In embodiments of the invention, the formulation is an emulsion, a suspension, a solution, a gel, a cream, a paste, a foam, a lubricant, a spray, a suppository, a pessary, or a tampon; the formulation is in or on a contraceptive device, such as a condom; the formulation further comprises an agent that inhibits conception, such as nonoxynol-9; and/or the formulation further comprises another antiviral agent, or an antibiotic agent (e.g., an antifungal agent or an antibacterial agent). The invention also relates to formulations, such as topical formulations, as above.

Another aspect of the invention is a complex comprising a polypeptide or conjugate of the invention and a viral envelope glycoprotein that comprises Man$_2$-A. Such a complex can form in vitro, and can be used, e.g., to further study the nature of the binding; or it can form in vivo, e.g., following administration of a polypeptide or conjugate of the invention to a subject infected with the virus.

Another aspect of the invention is an isolated polynucleotide, comprising a sequence encoding a polypeptide of the invention, which is operably linked to an expression control sequence. Optionally, the isolated polynucleotide further comprises a sequence that encodes an effector protein, which is operably linked to an expression control sequence. Embodiments of the invention include a vector comprising such a polynucleotide; a host cell comprising such a polynucleotide or vector; and a method for producing a polypeptide or conjugate of the invention (e.g., an antiviral polypeptide), comprising culturing the host cell as above, under conditions effective for expressing said polypeptide or conjugate, and, optionally, harvesting said polypeptide.

Another aspect of the invention is a kit suitable for carrying out a method of the invention, comprising one or more isolated polypeptides and/or conjugates of the invention. For example, a kit suitable for therapeutic or prophylactic treatment of a virus infection (e.g., an HIV infection) in a subject may further comprise a pharmaceutically acceptable carrier and, optionally, a container or packaging material. In a kit suitable for removing a virus (e.g., HIV) from a sample, the isolated polypeptide(s) and/or conjugate(s) may be attached to a solid support matrix.

In any of the methods of the invention, the virus which is inhibited, inactivated or removed is preferably HIV. In any of the compositions, including pharmaceutical compositions, conjugates, complexes, or methods of the invention, the isolated polypeptide is preferably a homodimer of a polypeptide represented by SEQ ID NO: 3.

The invention relates generally to MVL-like polypeptides, including active fragments or active variants of full-length, wild type MVL, examples of which are discussed below. An "MVL-like" polypeptide, as used herein, can refer, e.g., to a fall length, wild type MVL protein, or to an active fragment or variant of the wild type protein. MVL-like polypeptides are sometimes referred to herein as "polypeptides of the invention." It will be clear from context whether a particular "polypeptide of the invention" includes full-length, wild type MVL, e.g. as represented by SEQ ID NO: 3. Sometimes, for example when referring to a polypeptide per se, a "polypeptide of the invention" specifically excludes a fall-length, wild type MVL.

A polypeptide of the invention may be in the form of a monomer, or it may be in the form of a multimer, such as dimer, trimer, tetramer, octomer, dodecamer, or the like. The subunit portions of a multimer may be identical polypeptides (forming homo-multimers). Alternatively, different forms of a polypeptide (e.g., comprising different percent sequence identities to wild type MVL) may be "mixed and matched" to form hetero-multimers, provided the resulting multimer retains a measurable amount of an activity of a polypeptide of the invention. Preferably, the polypeptide is a homodimer. Much of the discussion herein is directed to a "polypeptide of the invention." It is to be understood that such discussion relates both to monomer and multimer forms of the polypeptide. It is known by skilled workers that lectins are able to overcome weak affinities with which they bind a given carbohydrate ligand through multimerization. For example, a mutant or variant form of a polypeptide of the invention that exhibits a low affinity of binding to an oligosaccharide comprising Man$_2$-A can attain high binding affinity when it is in the form of a multimer. This strategy increases both specificity, brought about by spacing of individual carbohydrate recognition domains, and overall avidity, brought about by multivalency (Mammen et al. (1998) *Angew. Chem. Int. Ed.* 37, 2754-2794; Kiessling et al. (1996) *Chem. Biol.,* 3, 71-77). One of skill in the art will recognize how to generate such multimers, and/or to increase the copy number of the carbohydrate binding sites represented by SEQ ID NOs: 1 and 2 in a single polypeptide chain. For example, one can make suitable recombinant tandem constructs, such as constructs comprising sequences encoding about two or more (or as many as about 3, 4, 6, 8, 10, 12 or more) tandem repeats of SEQ ID NO: 1; SEQ ID NO: 2; SEQ ID NO: 1 and SEQ ID NO: 2 separated by a suitable spacer; the entire 113 amino acid polypeptide; or combinations thereof.

One aspect of the invention is an isolated MVL-like polypeptide from the cyanobacterium, *Microcystis viridis* (preferably from the strain *Microcystis viridis* NIES-102), which binds specifically to an oligosaccharide comprising the tetrasaccharide Man-alpha-(1→6)Man-beta (1→4) GlcNAc-beta(1→4)GlcNAc (Man$_2$-A). In embodiments of the invention, the polypeptide does not comprise the sequence, SEQ ID NO: 3. Methods for isolating MVL-like polypeptides from *Microcystis viridis* bacteria, or from cells that express the polypeptide recombinantly, are discussed below.

As will be evident to a skilled worker, polypeptides of the invention bind with a similar specificity and affinity to a variety of oligosaccharides that comprise the above-mentioned tetrasaccharide, including, e.g., the oligosaccharides Man$_3$-A, Man$_6$, and Man$_9$ illustrated in FIG. 1, or any oligosaccharide comprising the tetrasaccharide of Man-2A or pentasaccharide of Man-3, which includes the majority of N-linked glycans of the so-called complex-type oligosaccharide group. Examples include bi-, tri-and tetra-antennary complex-type oligosaccharides decorated at the non-reducing ends with N-acetyl-glucosamine, galactose and sialic/neuraminic acid; that is, the known termini of known complex-type oligosaccharides. Furthermore, it is likely that polypeptides of the invention bind to and inhibit pathogens bearing as yet undetermined oligosaccharides that retain the Man-3 core.

The Examples herein show that polypeptides of the invention recognize with sub-micromolar affinity high mannose oligosaccharides, and bind the smaller ligands Man$_2$A and Man$_3$ with low micromolar affinities (<5 μM, Tables 1 and 2). The polypeptides do not bind to α-or β-linked di-mannosides or α-linked tri-mannosides that correspond to the D1, D2 and D3 arms of oligomannose-9; nor do they bind the disaccharides Manβ(1→4)GlcNAc and GlcNAcβ(1→4)GlcNAc or the trisaccharide mannotriose, each of which is present in the ubiquitous branching core of higher mannose structures. Furthermore, although the polypeptides bind oligomannose-2A and oligomannose-3 with equilibrium dissociation constants <5 μM, they do not bind with measurable affinities mixtures of the individual carbohydrates Manα(1→3)[Manα(1→6)]Manβ or GlcNAc$_2$ that together form oligomannose-3, even when these carbohydrates are added simultaneously to MVL in both NMR and ITC experiments.

A variety of organisms, including, of particular interest, infectious organisms, have on their surfaces (e.g., in envelopes, membranous surfaces, plasma membranes, or capsular structures) glycoproteins that comprise a Man$_2$-A tetrasaccharide, or other oligosaccharides as noted elsewhere herein, and thus can bind to polypeptides or conjugates of the invention. Thus, polypeptides or conjugates of the infection can inhibit the infectivity of such organisms. Often, but not necessarily, glycoproteins comprising an asparagine-linked glycosyl group comprise high mannose oligosaccharides; such high mannose oligosaccharides generally comprise, within the core, $Man_2$-A.

Among the many organisms that can be inhibited by polypeptides or conjugates of the invention are a variety of bacteria, parasites and viruses, particularly enveloped viruses. A skilled worker can readily determine, from published reports or from experimental studies, which organisms comprise the mentioned oligosaccharides on their surfaces, and thus can be inhibited by polypeptides or conjugates of the invention. The bacteria include, e.g., *chlamydia, legionella* or mycobacteria. The parasites include, e.g., protozoa (such as *Toxoplasma, Tritrichomonas*, Plasmodia, *Theilera, Trypanosoma*, etc.), flukes (such as *Schistosoma*), or the like. Other suitable infectious organisms include, e.g., spirochetes, kinetoplastida, actinomycetes, *treponema* and *borrelia*. Among the wide variety of suitable viruses are retroviral enveloped viruses, including, e.g., lentiviruses (such as HIV-1 and HIV-2), HTLV viruses (such as the human T-cell leukemia/lymphoma virus, HTLV-1, and HTLV-2), feline immunodeficiency virus (FIV), bovine immunodeficiency virus (BIV), and simian immunodeficiency virus (SIV). Among the non-retroviral enveloped viruses are herpesviruses (e.g., Herpes simplex viruses and HHV 6), measles virus (MV), influenza, and etiologic agents of hemorrhagic fevers. Viruses that can be inhibited by polypeptides or conjugates of the invention include, e.g., Type C and Type D retroviruses, Friend leukemia virus (FLV), murine leukemia virus (MLV), bovine leukemia virus (BLV), equine infectious virus, anemia virus, avian sarcoma viruses, such as Rous sarcoma virus (RSV), hepatitis viruses, such as hepatitis type A, B, non-A and non-B viruses, arboviruses, varicella viruses, or mumps and rubella viruses. Variants of any of such viruses, such as viruses which exhibit varying tropism or have evolved as a result of genetic drift, are included. Various strains of the viruses (including HIV), including primary isolates and laboratory-adapted strains, are included.

Preferably, a polypeptide of the invention binds to an oligosaccharide comprising $Man_2$-A with greater avidity than at about $10^{-6}$ to about $10^{-8}$ molar amounts, most preferably at nanomolar amounts (e.g., ranging from about $1 \times 10^{-9}$ to about $9 \times 10^{-9}$ molar). The polypeptide may take the form of a multimeric protein. As noted above, an individual, monomeric polypeptide of the invention (e.g., a mutant variant of wild type MVL) may, itself, exhibit sub-optimal binding affinity. However, a multimeric structure of this polypeptide may exhibit a much higher binding affinity, such as a nanomolar affinity.

Another aspect of the invention is an isolated polypeptide comprising one or more copies of the sequence GPLWSNX-EAQXXGPX (SEQ ID NO: 1) and/or one or more copies of the sequence FTGQWXTXVEXXMSV (SEQ ID NO: 2). Wild type MVL comprises two tandemly repeated homologous domains containing 54 amino acids with about fifty percent identity to one another. The two domains are separated in the wild type protein by a stretch of five amino acids. Within each of the two domains are one copy of SEQ ID NO: 1 (located at position 10-24 in the first domain and at position 69-83 of the second domain) and one copy of SEQ ID NO: 2 (located at position 33-47 in the first domain and at position 92-106 in the second domain); in each domain, SEQ ID NO: 1 and SEQ ID NO: 2 are separated from one another by a 9 amino acid spacer. The examples herein show that SEQ ID NO: 1 and SEQ ID NO: 2 are involved in binding to the mentioned carbohydrates.

Functional (active) MVL-like polypeptides may have more or fewer amino acids between the SEQ ID NO: 1 and SEQ ID NO: 2 sequences noted above, provided that the polypeptide retains its ability to bind to Manα(1→6)Manβ(1→4)GlcNAcβ(1→4)GlcNAc. Thus, the invention relates to isolated polypeptides in which the relative spacing of SEQ ID NO: 1 and SEQ ID NO: 2 is different from (longer or shorter than) that in the wild type protein, and/or to polypeptides in which the location of SEQ ID NO: 1 and/or SEQ ID NO: 2 is approximately, but not exactly, that as indicated above for the wild type polypeptide. For example, the first SEQ ID NO: 1 may be located at about position 7-20 at its N-terminus and about position 13-27 at its C-terminus, and the other conserved sequences will be shifted accordingly; or the first SEQ ID NO: 2 may be located at about position 66-79 at its N-terminus and about position 72-86 at its C-terminus, and the other conserved sequences will be shifted accordingly; etc. In a preferred embodiment, the SEQ ID NO: 1 and SEQ ID NO: 2 sequences are separated by a spacer of between about 6 and about 15 amino acids, or a functional equivalent thereof. Suitable functional equivalents include, e.g. linkers or spacer arms of the types described in US application 2002/0025317. One of skill in the art can readily design and test polypeptides which retain the desired activity, using conventional, routine procedures.

The invention relates to active fragments and/or variants of MVL. An "active" fragment or variant, as used herein, refers to a polypeptide which retains at least a measurable amount of a biological activity of MVL, e.g., specific and, preferably, high affinity binding, to an oligosaccharide comprising $Man_2$-A; the ability to inhibit infectivity or cytopathogenesis by a virus, such as HIV or other enveloped virus, e.g., as discussed herein; or the like. In general, the discussion herein refers to a "polypeptide of the invention" or an "MVL-like polypeptide." It is to be understand that active variants and/or fragments of MVL are also included.

The invention encompasses active fragments of MVL polypeptides. Such an "active fragment" can be from any portion of the polypeptide, and of any suitable size, provided that it retains a measurable amount of an activity of MVL. Preferably, the fragment comprises one or more copies of SEQ ID NO:1 and/or of SEQ ID NO: 2, or active fragments or variants of those sequences. Active fragments of the invention can lack one or more amino acids (e.g., 1, 2, 3, 4, 5, 6, 7, or more amino acids) from one or both ends of the fall-length molecule. In some embodiments, the fragment is considerably smaller than the full-length, wild type, molecule. For example, it can consist essentially of the sequence of SEQ ID NO: 1 or SEQ ID NO: 2; or one or both of these sequences, lacking some amino acid residues; or one or both of these sequences plus additional amino acids required to attain optimal structure for efficient function of the polypeptide. Functional fragments of about 15 amino acids are included in the invention. The term "polypeptide," as used herein, can be as small as, e.g., SEQ ID NO: 1 or SEQ ID NO: 2 and, as such, encompasses "peptides." It is well within the capacity of a skilled worker to generate fragments of MVL and to determine if a given fragment retains a requisite functional property of MVL. Examples of methods to assay for MVL properties or activities are discussed elsewhere herein.

Methods of preparing fragments of MVL are conventional. For example, one may clone a suitable polynucleotide and express such a fragment recombinantly; one may generate such a peptide synthetically; or one may cleave a full-length polypeptide, using suitable proteases or biochemical cleavage procedures. Combinations of these methods may also be used.

The invention also encompasses active variants of MVL polypeptides. The term, an "active variant" of a polypeptide, as used herein, refers to a polypeptide that comprises any of a variety of changes (alterations, modifications), either naturally occurring or deliberately generated, provided that the changes do not substantially alter normal activities of the polypeptide (i.e., provided that a variant polypeptide retains, to a measurable degree, at least one of the activities of the wild type polypeptide). The changes can be within a SEQ ID NO: 1 or a SEQ ID NO: 2 sequence; or they can be in other portions MVL which have been shown to be implicated in binding to the mentioned carbohydrates; or they can be in portions of the molecule that lie outside of the implicated binding regions. One of skill in the art can readily determine if a given variant retains an MVL activity, using conventional methods.

Variant polypeptides of the invention include polypeptides having one or more (e.g., 1, 2, 3, 4, 5, 6, 7 or more) naturally occurring (e.g., through natural mutation) or non-naturally-occurring (e.g., by deliberate modification, such as by site-directed mutagenesis) modifications, e.g., insertions, deletions, additions and/or substitutions, either conservative or non-conservative. By "conservative substitutions" is meant by combinations such as Gly, Ala; Val, Ile, Leu; Asp, Glu; Asn, Gln; Ser, Thr; Lys, Arg; and Phe, Tyr. Variants can include, e.g., homologs, muteins and mimetics. The invention also encompasses variants such as naturally occurring variants arising from alternative mRNA splicing events, and altered forms reflecting genetic polymorphism (e.g., allelic variation).

Active variants in which the spacing between SEQ ID NO: 1 and SEQ ID NO: 2 is varied are discussed above. Guidance as to which residues within or outside of the conserved domains (SEQ ID NO: 1 and SEQ ID NO: 2) can be altered without adversely affecting the binding of the polypeptide to the carbohydrate is provided with reference to FIGS. 2 and 7 and Example X. For example, the amino acids which are most strongly involved in binding to the carbohydrate (e.g., amino acids at positions 43 and 102) are probably more likely to be adversely affected by an alteration than are the amino acids which are least involved in binding (e.g., amino acids at positions 1-9, 15, 26-33, 35, 42, 50-66, 70, 74, 82, 84-91, 109-113). In general, variations of charged or polar amino acid residues are more likely to be deleterious than are variations at other residues. Further insight into which residues can withstand variation is provided by the finding that some of the residues are not at all conserved between the domains in each half of the polypeptide chain; and some (indicated in the alignment in FIG. 2 with single dots) are conserved but are not identical. The selection of a particular amino acid at these locations may be less constrained than the selection of an amino acid at a location in which the amino acids are identically conserved in the two repeats. In preferred variants of the invention, the residues which are most highly involved in binding to the carbohydrates, and which are most conserved between the repeated sequences, are not altered; whereas, for example, between about 1 and about 10; between about 1 and about 5; between about 1 and about 3; or more; of the other residues in the polypeptide are altered. Preferably, the altered amino acids are conservative substitutions, or amino acids that would not be expected to alter the structure of the polypeptide, or its interactions with the carbohydrate. Of course, some of the amino acids which lie outside of the conserved binding domains may be critical for the proper folding of the protein, and for achieving the proper structure for efficient carbohydrate binding, so not every one of such residues in the polypeptide can be altered. See the discussion in Example X for further guidance as to which residues of the polypeptide can be altered. It is well within the ability of a skilled worker to identify residues to alter, and to test the variant polypeptides for efficient binding activity, and/or for a biological function, such as the ability to inhibit viral infectivity.

Isolated naturally occurring allelic variants of MVL polypeptides are also encompassed by the invention.

Active variant MVL polypeptides of the invention may exhibit substantial identity to comparable portions of wild type MVL polypeptides. The entire polypeptide may be substantially identical to a wild type MVL, and/or the sequences of SEQ ID NO: 1 and/or SEQ ID NO: 2 may be substantially identical to the comparable region of the wild type protein. The term "substantial identity" or "substantial similarity" as used herein indicates that a polypeptide (or a nucleic acid) comprises a sequence that has at least about 90% sequence identity to a reference sequence, or preferably at least about 95%, or more preferably at least about 98% sequence identity to the reference sequence, over a comparison window of at least about 10 to about 100 or more amino acids residues or nucleotides. Methods to determine sequence identity (between nucleic acids or proteins) are conventional. Alignments can be accomplished by using any effective algorithm. For pairwise alignments of DNA sequences, the methods described by Wilbur-Lipman (e.g., Wilbur et al. (1983), *Proc. Natl. Acad. Sci.*, 80, 726-730) or Martinez/Needleman-Wunsch (e.g., Martinez (1983), *Nucleic Acid Res.* 11, 4629-4634) can be used. Pairs of protein sequences can be aligned by the Lipman-Pearson method (e.g., Lipman et al. (1985), *Science* 227, 1435-1441), e.g., with k-tuple set at 2, gap penalty set at 4, and gap length penalty set at 12. Various commercial and free sources of alignment programs are available, e.g., MegAlign by DNA Star, BLAST (National Center for Biotechnology Information), BCM (Baylor College of Medicine) Launcher, etc. Percent sequence identity can also be determined by other conventional methods, e.g., as described in Altschul et al. (1986), *Bull. Math. Bio.* 48, 603-616, 1986 and Henikoff et al. (1992), *Proc. Natl. Acad. Sci. USA* 89, 10915-10919.

An indication that two polypeptide sequences are substantially identical is that one protein is immunologically reactive with antibodies raised against the second protein. An indication that two nucleic acid sequences are substantially identical is that the polypeptide which the first nucleic acids encodes is immunologically cross reactive with the polypeptide encoded by the second nucleic acid.

Other types of variant polypeptides of the invention include one or more of various types of protein modifications, including post-translational modifications. Post-translational modifications include naturally occurring or synthetically produced, covalent or aggregative conjugates with other chemical moieties, e.g., glycosyl groups, lipids, phosphates, acetyl groups, etc., as well as cleavage, such as of terminal amino acid(s). See, e.g., modifications disclosed in U.S. Pat. No. 5,935,835. A variety of chemical modifications may be introduced which enhance the stability of a polypeptide or conjugate of the invention. See, e.g. Wunsch (1983) *Biopolymers* 22, 493-505 and Samanen, in Polymeric Materials in Medication, Gebelein et al, eds, Plenum Press: New York, 1985, pp. 227-242. Among possible options for useful chemical modifications include, e.g., olefin substitution, carbonyl reduction, D-amino acid substitution, N-methyl substitution, C-methyl substitution, C—C'-methylene insertion, dehydro amino acid insertion, retro-inverso modification, N-terminal to C-terminal cyclization, and thiomethylene modification. Polypeptides of the invention and conjugates thereof can also be modified by covalent attachment of carbohydrates and polyoxyethylene derivatives, which are expected to enhance stability and resistance to proteolysis. See, e.g., Abuchowski et al., in Enzymes as Drugs, Holcenberg et al., eds, John Wiley: New York, 1981, pp. 367-378. Other active variants may comprise added peptide sequences, either naturally occurring or heterologous, such as, e.g., leader, signal, secretory, targeting, enzymatic etc. sequences.

As used herein, the term "protein" is interchangeable with "polypeptide" or "peptide." A polypeptide can be of any length that is compatible with the invention, including being a short peptide. For example, suitable polypeptides can be between about 5 and about 20 amino acids in length, e.g., about 15 amino acids (the length of SEQ ID NO: 1 or SEQ ID NO: 2).

Polypeptides of the invention can be prepared by a variety of procedures, which will be evident to a skilled worker. For example, MVL polypeptides can be harvested from natural sources, such as *Microcystis viridis* (e.g., *Microcystis viridis* NIES-102) bacteria. In another embodiment, polypeptides of the invention are harvested from cells (e.g., bacteria) that are transformed or transfected with a nucleic acid encoding MVL or an active fragment or variant thereof, wherein the nucleic acid is operatively linked to an expression control sequence. Under suitable conditions, which will be evident to the skilled worker, the polypeptide is expressed in the cell. Following harvest and optional purification, polypeptides of the invention can be used in methods of the invention; or they can be further modified and/or used to form conjugates of the invention. Suitable growth conditions for culturing the bacteria so that MVL polypeptides are produced are conventional. For example, anaerobic growth conditions for *Microcystis viridis* are described in Boyd et al., 1997, supra. Conventional methods can be used to isolate and, optionally, purify the proteins. For example, using conventional bioassays, e.g., for HIV activity, one can develop bioassay-guided strategies of purification. Suitable bioassays include, e.g., monitoring the protection of cells, such a T-lymphoblastoid cells, from HIV-1 induced cell killing, as measured by an XTT-tetrazolium anti-HIV assay (see, e.g., Gulakowski et al. (1991) *J. Virol. Methods* 33, 87-100), or other conventional assays, e.g., as described in O'Keefe et al. (1997) *Eur. J. Biochem* 245, 47-53 and Buckheit et al. (1994) *AIDS Res. Hunt. Retroviruses* 10, 1497-1506. See also the Examples herein. Some methods for isolating and, optionally, purifying the polypeptides are discussed below.

One method for preparing a polypeptide of the invention is to clone a nucleic acid encoding the polypeptide into a vector, introduce the vector into a suitable prokaryotic or eukaryotic host cell, culture the cell under conditions effective for expression of the polypeptide, and harvest the polypeptide from the cell. Suitable host cells include, e.g., bacteria, yeast, insects, mammalian or plant cells. The recombinant polypeptide can also be expressed in a transgenic plant or non-human animal. Methods for cloning and expressing polypeptides are routine and conventional. For general references describing methods of molecular biology which are mentioned in this application, e.g., isolating, cloning, modifying, labeling, manipulating, sequencing and otherwise treating or analyzing nucleic acids and/or proteins, see, e.g., Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc.

Methods of producing proteins in transgenic plants and animals are disclosed, e.g., in Hogan et al., (1986) *Manipulating The Mouse Embryo*, Cold Spring Harbor Press; Krimpenfort et al., (1991) *Bio/Technology* 9, 86; Palmiter et al., (1985) *Cell* 41, 343; Kraemer et al., (1985) *Genetic Manipulation of The Early Mammalian Embryo*, Cold Spring Harbor Laboratory Press; Hammer et al., (1985) *Nature* 315, 680; Purcel et al., (1986) *Science* 244, 1281; Wagner et al., U.S. Pat. No. 5,175,385; and Krimpenfort et al, U.S. Pat. No. 5,175,384.

In a preferred embodiment, a sequence coding for an MVL polypeptide of the invention is placed under the control of an expression control sequence. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

Suitable expression control sequences can be selected for host compatibility and desired purpose. These include, e.g., enhancers such as from SV40, CMV, RSV, inducible or constitutive promoters, and cell-type specific elements or sequences which allow selective or specific cell expression. Promoters that can be used to drive expression, include, e.g., an endogenous promoter, MMTV, SV40, CMV, c-fos, β-globin; trp, lac, tac, or T7 promoters for bacterial hosts; or alpha factor, alcohol oxidase, or PGH promoters for yeast. See, e.g., Melton et al., (1984) *Polynucleotide Res.,* 12(18), 7035-7056; Dunn et al. (1984), *J. Mol. Bio.,* 166, 477-435; U.S. Pat. No. 5,891,636; Studier et al. (1987), Gene Expression Technology, *Methods in Enzymology,* 85, 60-89. In addition, as discussed above, translational signals (including in-frame insertions) can be included. A natural expression control sequence of a gene may be used to express the protein recombinantly, e.g., an MVL expression control sequence can be used to drive the expression of a recombinant polypeptide of the invention.

As used herein, the term "conditions effective for expression" of a polypeptide means, in part, that the nucleic acid encoding it comprises expression control sequences that allow transcription of a DNA into RNA and translation of an RNA into a polypeptide. Effective conditions for expression of a protein include any conditions which are suitable for achieving production of the protein, including effective temperatures, pH, salts, or the like.

A polynucleotide of the present invention can be cloned into any suitable vector. A vector is, e.g., a polynucleotide molecule which can replicate autonomously in a host cell, e.g., containing an origin of replication. In some embodiments, additional art-recognized elements, which aid in the selection of a plasmid in a cell, amplification of the plasmid, etc. are present. When expression of a protein is desired, an expression vector, comprising effective expression control sequences, can be used. A skilled worker can select a vector depending on the purpose desired, e.g., to propagate and/or express the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54 0, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRMII/TOPO, pCR4/TOPO, pTrcHisB, pCMV6-XL4, etc. However, any other vector, e.g., plasmids, viruses, or parts thereof, may be used as long as they are replicable and viable in the desired host.

The cloned nucleic acids, in a suitable vector, can be "introduced" into a cell by any of a variety of conventional, art-recognized procedures, including, e.g., transfection (e.g., mediated by DEAE-Dextran or calcium phosphate precipitation), infection via a viral vector (e.g., retrovirus, adenovirus, adeno-associated virus, lentivirus, pseudotyped retrovirus or poxvirus vectors), injection, electroporation, sonoporation, a gene gun, liposome delivery (e.g., Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), or other liposomes developed according to procedures standard in the art), or receptor-mediated and other endocytosis mechanisms.

In one embodiment of the invention, the MVL polypeptide is further isolated (e.g., purified) from other components of the cell (e.g., from other components of a cell extract). Methods for harvesting a polypeptide from a cell are conventional. For example, cells can be scraped from a plate, centrifuged if grown in culture medium, etc., and the cells can be lysed to generate crude cell extracts, using conventional procedures. Alternatively, a cell can be engineered so that a recombinant polypeptide is secreted into the culture medium, and the polypeptide can be harvested from the medium. Any suitable combination of isolation or purification methods can be used to further isolate (e.g., purify) a polypeptide from a crude lysate. In embodiments of the invention, the MVL polypeptide is substantially purified or is purified to homogeneity. By "substantially purified" is meant that the polypeptide is separated and is essentially free from other polypeptides, i.e., the polypeptide is the primary and active constituent.

Methods of performing isolations (e.g., purifications) of polypeptides are conventional. Among the biochemical purification procedures known to those of skill in the art are, e.g., detergent extraction (e.g., non-ionic detergent, Triton X-100, CHAPS, octylglucoside, Igepal CA-630); differential solubility (e.g., ammonium sulfate or ethanol precipitation, acid extraction); centrifugation; isoelectric focusing; gel electrophoresis; and chromatography (e.g., anion or cation exchange chromatography, phosphocellulose chromatography, hydrophobic interaction chromatography, hydroxyapatite chromatography, high performance liquid chromatography (HPLC), lectin chromatography, affinity column chromatography). Protein refolding steps can be used, as necessary, in completing the configuration of the mature protein.

In one embodiment, a recombinant MVL polypeptide is produced as a fusion protein in frame with an epitope tag (such as, e.g., haemagglutinin (HA), FLAG, myc, 6xHis (SEQ ID NO: 7), maltose binding protein, chitinase, etc.), and the fusion protein is selectively isolated with an antibody specific for the tag. The isolation can be performed by immunoprecipitation, with antibody columns (antibody-conjugated affinity chromatography), with antibodies bound to magnetic beads, or other conventional techniques. Methods of constructing, expressing and isolating (e.g., purifying) such recombinant fusion proteins are conventional and are discussed elsewhere herein.

In one embodiment, a polypeptide of the invention is produced synthetically, using conventional procedures. Combinations of recombinant and synthetic procedures may also be used.

Another aspect of the invention is a conjugate of an MVL protein or a polypeptide of the invention and an effector molecule. For example, the specificity and binding avidity of polypeptides of the invention for, e.g., enveloped viruses, such as HIV, and/or cells infected with such viruses, allows the polypeptides to target the viruses or cells and to deliver to them agents (effectors) that can further inhibit viral infectivity and/or cytopathogenicity. That is, conjugates can be designed that bind to viruses or virus-expressing cells (e.g., via interaction with gp120) and destroy them. In other embodiments, effectors conjugated to polypeptides of the invention enhance the activity of the polypeptides, e.g., by stabilizing them.

Suitable effector molecules include toxins or immunological agents. Among the many suitable toxins are, e.g., a *Pseudomonas* exotoxin, such as *Pseudomonas* exotoxin A (PE40), diphtheria toxin, ricin A-chain or B-chain, botulina toxin, pokeweed antiviral protein, and others that will be evident to skilled workers. Toxic radionuclides can also be used, for methods of radiotherapy. An "immunological agent" includes an antibody, immunoglobulin, or immunological recognition element. An "immunological recognition element," as used herein, refers to an element, such as a peptide, e.g., a FLAG sequence, which facilitates, through immunological recognition, isolation and/or purification and/or analysis of the polypeptide to which it is attached. Effector molecules that can be used include molecules that enhance placental transfer, or that effect a targeted recruitment of immunological mechanisms of pathogen elimination, such as phagocytic engulfment and killing by antibody-dependent cell-mediated cytotoxicity.

Other effector components can include, for example, agents that improve stability of the polypeptide; increase the half-life of the polypeptide; increase resistance of the polypeptide to proteolysis; decrease the immunogenicity of the polypeptide; decrease the rate of in vivo clearance of the polypeptide; provide a means to attach or immobilize a polypeptide or conjugate of the invention onto a solid support matrix (see, e.g., Harris, in Poly(Ethylene Glycol) Chemistry: Biotechnical and Biomedical Applications, Harris, ed., Plenum Press: New York (1992), pp. 1-14); or the like. Suitable such agents include, e.g., polyethylene glycol, dextran, albumin, etc.

Conjugates of the invention can comprise a polypeptide of the invention coupled to more than one effector molecule, each of which, optionally, can have different effector functions, such as a toxin molecule (or an immunological reagent) and a polyethylene glycol, dextran, or albumin molecule.

In general, suitable effector molecules exert their effect outside of a target cell. In some embodiments, the effector molecule functions within a target cell; in these embodiments, the effector molecule is attached to the polypeptide of the invention by a labile bond, examples of which will be evident to a skilled worker.

In one embodiment, a conjugate of the invention is produced by recombinant DNA technology, as discussed elsewhere herein. Alternatively, the conjugate can be produced by chemical coupling of a polypeptide of the invention with an effector molecule as described above. Procedures for covalent attachment of molecules, such as polyethylene glycol, dextran, albumin and the like, to proteins, are well-known to those skilled in the art, and are extensively documented in the literature (e.g., see Davis et al., In Peptide and Protein Drug Delivery, Lee, ed., Marcel Dekker: New York, 1991, pp. 831-864 and PCT/US00/06588).

Another aspect of the invention is a polynucleotide encoding a polypeptide or conjugate of the invention. Some such polynucleotides are discussed above, with regard to recombinant technology. As used herein, the terms "nucleic acid" and "polynucleotide" are interchangeable. A nucleic acid or polynucleotide can be of any length that is compatible with the invention, including being a very short oligonucleotide.

Nucleic acids encoding an MVL polypeptides of the invention may differ from wild type sequences (be "variant" sequences), provided that the encoded polypeptide retains a measurable amount of one or more activities characteristic of the wild type polypeptide. For example, a variant nucleic acid may contain one or more naturally or non-naturally occurring modifications (e.g., insertions, deletions, additions, substitutions, inversions, etc.), mutations, polymorphisms, etc.; or the nucleic acid may differ from its wild type counterpart with regard to base composition, reflecting the degeneracy of the genetic code. Other variants may be substantially identical to a wild type sequence, e.g., a nucleic acid may comprise a sequence that has at least about 90% sequence identity to a reference sequence, or preferably at least about 95%, or more preferably at least about 98% to the reference sequence, over a comparison window of at least about 10 to about 100 or more nucleotides.

Furthermore, a polynucleotide variant may comprise additional polynucleotide sequences, e.g., sequences to enhance expression, detection, uptake, cataloging, tagging, etc. For example, the polynucleotide may contain additional non-naturally occurring or heterologous coding sequences (e.g., sequences coding for leader, signal, secretory, targeting, enzymatic, fluorescent, antibiotic resistance, and other functional or diagnostic peptides) or non-coding sequences (e.g., untranslated sequences at either a 5' or 3' end, or dispersed in the coding sequence, such as introns).

Nucleic acids encoding a polypeptide sequence of the invention can be obtained by conventional procedures, e.g., they can be obtained from commercial sources; cleaved from larger polynucleic acids, such as genomic DNA, with appropriate restriction enzymes; generated as cDNAs with reverse transcriptases; amplified by PCR or similar procedures; or produced, at least in part, with the use of automated DNA synthesizers. Combinations of these methods may also be used.

Polypeptides or conjugates of the invention can be used for inhibiting infection of a host by any organism whose surface comprises the tetrasaccharide, $Man_2A$. The host (e.g., subject or patient) may be any animal which experiences a condition mediated by an infectious organism that can be inhibited by a polypeptide or conjugate of the invention.

Suitable subjects include, e.g., a cat, dog, horse, bird, rodent, non-human primate or human. Examples of suitable infectious organisms are noted elsewhere herein. In preferred embodiments, the organism is an enveloped virus, such as a retrovirus, in particular an immunodeficiency virus, such as HIV, specifically HIV-1 and HIV-2. The method can treat, inhibit, or prevent infection or cytopathology and/or can ameliorate symptoms associated with such infections. The polypeptides or conjugates can be administered to subjects that are infected with a virus (therapeutic) or that are at risk for viral infection (prophylactic).

In one embodiment, the method comprises administering to a subject an antiviral effective amount of an above-described polypeptide or conjugate. In one embodiment, the polypeptide or conjugate is attached to a solid support matrix. Upon administration of the antiviral effective amount of the conjugate, the viral infection is inhibited.

In another embodiment, the method comprises inhibiting (e.g., preventing) sexual transmission of viral infection, e.g., HIV infection, comprising vaginal, rectal, oral, penile, or other topical, insertional, or instillational treatment with an antiviral effective amount of a polypeptide and/or conjugate of the invention, and/or a viable host cell transformed to express a polypeptide or conjugate of the invention, alone or in combination with another antiviral compound.

Polypeptides or conjugates of the invention can also be used to treat inanimate objects or materials, such as medical equipment or supplies; or to treat (e.g., ex vivo) a bodily product or tissue, including biological fluids, such as blood, blood products and vaccine formulations, cells, tissues and organs, to remove or inactivate virus in an effort to prevent or treat viral infection of an animal, such as a human. The compositions can also be used to treat any solution, suspension, emulsion or other material to remove or inactivate such a virus. In general, the terms "remove" and "inactivate" a virus, as used herein, encompass removing or inactivating a detectable amount of the virus. In a preferred embodiment, the amount of virus that is removed or inactivated is a substantial amount, e.g. at least about 50%, 75%, 90% etc. of the virus.

A number of considerations are generally taken into account in designing delivery systems, routes of administration, and formulations for protein and peptide drugs, such as the polypeptides and conjugates of the invention. See, e.g., Eppstein (1988), *CRC Crit. Rev. Therapeutic Drug Carrier Systems* 5, 99-139; Siddiqui et al. (1987), *CRC Crit. Rev. Therapeutic Drug Carrier Systems* 3, 195-208, 1987); Banga et al. (1988), *Int. J. Pharmaceutics* 48, 15-50; Sanders (1990), *Eur. J. Drug Metab. Pharmacokinetics* 15, 95-102; and Verhoef (1990), *Eur. J. Drug Metab. Pharmaco-kinetics* 15, 83-93. The appropriate delivery system for a given polypeptide or conjugate of the invention will depend upon its particular nature, the particular clinical application, and the site of drug action. As with any protein or peptide drug, oral delivery of a polypeptide or conjugate of the invention will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it is preferable to use an absorption-enhancing agent in combination with a given polypeptide or conjugate of the invention. A wide variety of absorption-enhancing agents have been investigated and/or applied in combination with protein and peptide drugs for oral delivery and for delivery by other routes (Verhoef, 1990, supra; van Hoogdalem (1989), *Pharmac. Ther.* 44, 407-443; Davis, J. (1992) *Pharm. Pharmacol.* 44 (Suppl. 1), 186-190). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs, such as the polypeptides and conjugates of the invention, can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as polypeptides or conjugates of the invention, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in Microencapsulation and Related Processes, Swarbrick, ed., Marcell Dekker, Inc.: New York, 1984, pp. 1-60, 88-89, 208-211). Microcapsules also can provide a useful way to effect a prolonged delivery of a protein and peptide drug, such as a polypeptide or conjugate of the invention, after injection (Maulding, J. (1987) *Controlled Release* 6, 167-176).

Given the aforementioned potential complexities of successful oral delivery of a protein or peptide drug, it is fortunate that there are numerous other potential routes of delivery of a protein or peptide drug, such as a polypeptide or conjugate of the invention. These routes include intravenous, intraarterial, intrathecal, intracisternal, intramuscular, intraperitoneal, buccal, rectal, nasal, pulmonary, transdermal, vaginal, ocular, transdermal, extracorporeal, and the like (See, e.g., Eppstein, 1988, supra; Siddiqui et al., 1987, supra; Banga et al., 1988, supra; Sanders, 1990, supra; Verhoef, 1990, supra; Barry, in Delivery Systems for Peptide Drags, Davis et al., eds., Plenum Press: New York, 1986, pp. 265-275; and Patton et al. (1992), *Adv. Drug Delivery Rev.* 8, 179-196). In a preferred embodiment, topical administration is used e.g., vaginal, rectal, penile, to the mouth, or other topical treatment with an antiviral effective amount of a polypeptide and/or conjugate of the invention.

With any of these routes, or, indeed, with any other route of administration or application, a protein or peptide drug, such as a polypeptide or conjugate of the invention, may initiate an immunogenic reaction. In such situations it may be preferable to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al. 1981, supra; Abuchowski et al. (1977), *J. Biol. Chem.* 252, 3578-3581; Lisi et al. (1982), *J. Appl. Biochem.* 4, 19-33, 1982; and Wileman et al. (1986), *J. Pharm. Pharmacol.* 38, 264-271). Such modifications also can have advantageous effects on stability and half-life both in vivo and ex vivo.

Other strategies to avoid untoward immune reactions can also include the induction of tolerance by administration initially of only low doses. In any event, it will be apparent from the present disclosure to one skilled in the art that for any particular desired medical application or use of a polypeptide or conjugate of the invention, the skilled artisan can select from any of a wide variety of possible compositions, routes of administration, or sites of application, what is advantageous.

It will also be appreciated by one skilled in the art that a DNA sequence of a polypeptide or conjugate of the present invention can be inserted ex vivo into mammalian cells previously removed from a given animal, in particular a human, host. Such cells can be employed to express the corresponding polypeptide or conjugate in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al. (1994) *AIDS Res. Hum. Retrovir.* 10, 1507-1515). As an alternative to ex vivo insertion of the DNA sequences of the present invention, such sequences can be inserted into cells directly in vivo, such as by use of an appropriate viral vector. Such cells transfected in vivo are expected to produce antiviral amounts of a polypeptide or a conjugate of the invention directly in vivo.

It will be additionally appreciated that a DNA sequence corresponding to a polypeptide or conjugate of the invention can be inserted into suitable nonmammalian host cells (such as a bacterium or yeast cell), and that such host cells will express therapeutic or prophylactic amounts of the polypeptide or conjugate directly in vivo within a desired body compartment of an animal, in particular a human.

In a preferred embodiment of the present invention, a method of female-controllable prophylaxis against HIV infection comprises the intravaginal administration and/or establishment of, in a female human, a persistent intravaginal population of lactobacilli that have been transformed with a coding sequence of the present invention to produce, over a prolonged time, effective virucidal levels of a polypeptide or conjugate of the invention, directly on or within the vaginal and/or cervical and/or uterine mucosa. It is noteworthy that both the World Health Organization (WHO), as well as the U.S. National Institute of Allergy and Infectious Diseases, have pointed to the need for development of female-controlled topical microbicides, suitable for blocking the transmission of HIV, as an urgent global priority (Lange et al. (1995), *Lancet* 341, 1356; Fauci (Apr. 27, 1995), *NIAID News*, Apr. 27). A composition comprising a present inventive antiviral agent and a solid-support matrix is particularly useful in this regard, particularly when the solid-support matrix is a contraceptive device, such as a condom, a diaphragm, a cervical cap, a vaginal ring, a dental dam, or a sponge.

The antiviral polypeptides and conjugates of the invention can be formulated into various compositions, e.g., pharmaceutical compositions, for use, for example, either in therapeutic treatment methods for infected individuals, or in prophylactic methods against viral, e.g., HIV, infection of uninfected individuals.

The composition can comprise a carrier, such as a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18 th ed., Mack Publishing Company, 1990.

A pharmaceutical composition of the invention can contain other pharmaceuticals, in conjunction with the polypeptide or conjugate of the invention, particularly when used to therapeutically treat a viral infection, such as one which results in AIDS. Representative examples of these additional pharmaceuticals include antiviral compounds, virucides, immunomodulators, immunostimulants, antibiotics, absorption enhancers, and agents that inhibit contraception (such as nonoxynol-9). Exemplary antiviral compounds include AZT, ddI, ddC, gancyclovir, acyclovir, fluorinated dideoxynucleosides, nonnucleoside analog compounds, such as nevirapine (Shih et al. (1991), PNAS 88, 9878-9882), TIBO derivatives, such as R82913 (White et al. (1991), Antiviral Res. 16, 257-266), BI-RJ-70 (Merigan (1991), Am. J. Med. 90 (Suppl. 4A),8S-17S), michellamines (Boyd et al., (1994) J. Med. Chem. 37, 1740-1745), calanolides (Kashman et al. (1992), J. Med. Chem. 35, 2735-2743), nonoxynol-9, gossypol and derivatives, gramicidin (Bourinbair et al., 1994, supra), and Ro 31-8959. Exemplary immunomodulators and immunostimulants include various interleukins, recombinant sCD4, cytokines (including α-interferon), antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids (Davis, 1992, supra).

One skilled in the art will appreciate that the particular formulation will depend, in part, upon the particular polypeptide or conjugate of the invention employed, and the chosen route of administration. Accordingly, there is a wide variety of suitable formulations of the composition of the present invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al. (1993), Science 260, 912-915).

The polypeptides or conjugates of the invention, alone or in combination with other antiviral compounds, can be made into aerosol formulations to be administered via inhalation. These aerosol formulations can be placed into pressurized acceptable propellants, such as dichlorodifluoromethane, propane, nitrogen and the like.

The polypeptides or conjugates of the invention, alone or in combinations with other antiviral compounds or absorption modulators, can be made into suitable formulations for transdermal application and absorption (Wallace et al., 1993, supra). Transdermal electroporation or iontophoresis also can be used to promote and/or control the systemic delivery of the compounds and/or compositions of the present invention through the skin (e.g., see Theiss et al. (1991), Meth. Find. Exp. Clin. Pharmacol. 13, 353-359).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, pessaries, tampons or the like. The formulations may contain, for example, freeze-dried bacteria, such as lactobacilli, that are genetically engineered to directly produce a polypeptide or conjugate of the present invention.

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such as, for example, freeze-dried lactobacilli genetically engineered to directly produce a polypeptide or conjugate of the present invention, carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, a dental dam, or a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a polypeptide or conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations.

Formulations suitable for ex vivo sterilization or removal of virus, such as infectious virus, from a sample, such as a bodily product (e.g., blood, blood products, sperm, fluids, cells, tissues or organs), or any other solution, suspension, emulsion, vaccine formulation, or any other material which can be administered to a patient in a medical procedure, can be selected or adapted as appropriate by one skilled in the art, from any of the aforementioned compositions or formulations.

One skilled in the art will appreciate that a suitable or appropriate formulation can be selected, adapted or developed based upon the particular application at hand.

Dosages for administration of a polypeptide or conjugate of the invention can be in unit dosage form, such as a tablet or capsule. The term "unit dosage form" as used herein refers to physically discrete units suitable as unitary dosages for human and animal subjects, each unit containing a predetermined quantity of a polypeptide or conjugate of the invention, alone or in combination with other antiviral agents, calculated in an amount sufficient to produce the desired effect in association with a pharmaceutically acceptable diluent, carrier, or vehicle.

The specifications for the unit dosage forms of the present invention depend on the particular polypeptide or conjugate of the invention, or composition thereof, employed and the effect to be achieved, as well as the pharmacodynamics associated with each polypeptide or conjugate, or composition thereof, in the host. In some embodiments, the dose administered is an "antiviral effective amount" or an amount necessary to achieve an "effective level" in the individual patient.

Since the "effective level" is used as the preferred endpoint for dosing, the actual dose and schedule can vary, depending upon individual differences in pharmacokinetics, drug distribution, and metabolism. The "effective level" can be defined, for example, as the blood or tissue level (e.g., about 0.1-1000 nM) desired in the patient that corresponds to a concentration of one or more polypeptide or conjugate of the invention, which inhibits a virus, such as HIV, in an assay known to predict for clinical antiviral activity of chemical compounds and biological agents. The "effective level" for agents of the present invention also can vary when the polypeptide or conjugate of the invention, or composition thereof, is used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a "mega-dosing" regimen, wherein a large dose of the polypeptide or conjugate of the invention is administered, time is allowed for the drug to act, and then a suitable reagent is administered to the individual to inactivate the drug.

Administration of a polypeptide or conjugate of the invention with other anti-retroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between about 0.05 m$\mu$M and about 1.0 m$\mu$M. A range of about 0.005-0.25 mg/kg body weight is virustatic in most patients. The preliminary dose ranges for oral administration are somewhat broader, for example about 0.001 to about 0.25 mg/kg given in one or more doses at intervals of 2, 4, 6, 8, 12, etc. hours. Currently; about 0.01 mg/kg body weight ddC given every about 8 hrs is preferred. When given in combined therapy, the other antiviral compound, for example, can be given at the same time as the polypeptide or conjugate of the invention or the dosing can be staggered as desired. The two drugs also can be combined in a composition. Doses of each can be less when used in combination than when either is used alone.

For ex vivo uses, such as virucidal treatments of inanimate objects or materials, blood or blood products, or tissues, the amount of polypeptide or conjugate of the invention, or composition thereof, to be employed should be sufficient that a detectable amount of, preferably most of, and most preferably all of, any virus or virus-producing cells present will be rendered noninfectious or will be destroyed. For example, for HIV, this would require that the virus and/or the virus-producing cells be exposed to concentrations of the polypeptide in the range of about 0.1 to about 1000 nM. Similar considerations apply to in vivo applications, which are discussed more fully below. Therefore, the designation of an "effective amount" or an "antiviral effective amount" is used generally to describe the amount of a particular polypeptide or conjugate of the invention, or composition thereof, required for at least a detectable amount of antiviral efficacy in any given application.

For in vivo uses, the dose of a polypeptide or conjugate of the invention, or composition thereof, administered to an animal, particularly a human, in the context of the present invention should be sufficient to effect a prophylactic or therapeutic response in the individual over a reasonable time frame. In general, preferred times for administration are at the pre-entry/entry stage (e.g., pre-and post-fusogenic stages, such as gp41-mediated fusion). The exact amount of the dose will vary from subject to subject, depending on the species, age, weight and general condition of the subject, the severity or mechanism of any disorder being treated, the particular agent or vehicle used, its mode of administration and the like. The dose used to achieve a desired antiviral concentration in vivo (e.g., about 0.1-1000 nM) will be determined by the potency of the particular polypeptide or conjugate employed, the severity of the disease state of infected individuals, as well as, in the case of systemic administration, the body weight and age of the infected individual. The size of the dose also will be determined by the existence of any adverse side effects that may accompany the particular polypeptide or conjugate of the invention, or composition thereof, employed. It is generally desirable, whenever possible, to keep adverse side effects to a minimum.

The present invention also provides polypeptides or conjugates of the invention that are attached to a solid support matrix. "Attached" is used herein to refer to attachment to (or coupling to) and immobilization in or on the solid support matrix. While any means of attachment can be used, attachment is preferably by covalent bonds. Such a support matrix can, e.g., facilitate contacting or binding virus (e.g., infectious virus) in a sample or removing virus (e.g., infectious virus) from a sample. The sample can be, e.g., a bodily product such as a fluid, cells, a tissue or an organ from an organism, in particular a mammal, such as a human, including, for example, blood, a component of blood, or sperm. The solid support matrix may comprise magnetic beads, to facilitate contacting, binding and removal of a virus, and to enable magnet-assisted removal of the virus from a sample as described above. Alternatively, the solid support matrix may comprise a flow-through matrix, which may have, e.g., a configuration similar to an affinity column; or it may comprise a porous surface or membrane, over or through which a sample is flowed or percolated, thereby selectively entrapping or removing virus (e.g., infectious virus) from the sample. In another embodiment, the solid support matrix comprise a condom, a diaphragm, a cervical cap, a vaginal ring, a dental dam, a sponge, or the like.

For any given formulation or composition comprising a polypeptide or conjugate of the invention that is attached to or immobilized on a solid support matrix, the formulation or composition preferably retains the desired (i.e., in this instance, the virus binding (e.g., gp120-binding) and virus-inactivating (e.g., HIV)) properties of the polypeptide or conjugate, itself.

The present invention provides a method of removing virus, such as a retrovirus, e.g., HIV, from a sample. The sample can be any material, including those discussed herein, e.g., blood, sperm, cells, tissues, organs, or any solution, suspension, emulsion or other material. The method comprises contacting the sample with a composition comprising an isolated and, optionally, purified antiviral polypeptide or conjugate of the invention, wherein at least a portion of the polypeptide binds specifically to the virus. The contacting is performed under conditions effective for binding of the virus in the sample to the polypeptide or conjugate. "Effective conditions" include suitable salt, pH, temperature, etc. conditions which result in the desired specific binding. Such conditions can be determined empirically, following routine procedures. Preferably, the antiviral polypeptide or conjugate is attached to a solid support matrix, e.g., as described above. The method further comprises separating the sample and the composition by any suitable means, whereupon the virus, such as infectious virus, is removed from the sample. Such methods can be used in real time ex vivo removal of virus or virus infected cells from a bodily fluid, such as blood, e.g., in the treatment of viral infection, or in the removal of virus from blood or a component of blood, e.g., for transfusion, in the inhibition or prevention of viral infection. Such methods also have potential utility in dialysis, such as kidney dialysis.

In one embodiment, the antiviral polypeptide is attached to a matrix with an antibody specific for a polypeptide of the invention or for an effector; this method of attachment is discussed further below. In another embodiment, the solid support matrix is coated with streptavidin and the antiviral polypeptide is biotinylated. Through biotin, the biotinylated antiviral protein/peptide is attached to the streptavidin-coated solid support matrix. Other types of means, as are known in the art, can be used to attach a functional polypeptide (i.e., an antiviral polypeptide) or conjugate of the invention to a solid support matrix. The choice of solid support matrix, means of attachment of the functional polypeptide to the solid support matrix, and means of separating the sample and the matrix-anchored polypeptide will depend, in part, on the sample (e.g., fluid vs. tissue) and the virus to be removed. It is expected that the use of a selected coupling molecule can confer certain desired properties to a matrix, comprising a functional polypeptide of the invention coupled therewith, that may have particularly advantageous properties in a given situation.

The skilled practitioner might select a poly(ethylene glycol) molecule for attaching a functional polypeptide of the invention to a solid support matrix, thereby to provide a matrix-anchored polypeptide, wherein the polypeptide is attached to the matrix by a longer "tether" than would be feasible or possible for other attachment methods, such as biotinylation/streptavidin coupling. A polypeptide of the invention coupled by a poly(ethylene glycol) "tether" to a solid support matrix (such as magnetic beads, porous surface or membrane, and the like) can permit optimal exposure of a binding surface, epitope, hydrophobic or hydrophobic focus, and/or the like, on a functional polypeptide of the invention in a manner that, in a given situation and/or for a particular virus, facilitates the binding and/or inactivation of the virus. Diverse applications and uses of proteins and peptides, such as the polypeptides and conjugates of the invention, attached to or immobilized on a solid support matrix, are exemplified for poly(ethylene glycol) conjugated proteins or peptides in a review by Holmberg et al. (In Poly(Ethylene Glycol) Chemistry: Biotechnical and Biomedical Applications, Harris, ed., Plenum Press: New York, 1992, pp. 303-324).

In methods as above, polypeptides and conjugates of the invention bind substantially irreversibly to virus, such as immunodeficiency virus, e.g., HIV, specifically HIV-1 or HIV-2. Thus, the viral particle is substantially permanently fixed to the antiviral agent and is removed from the sample, thereby rendering it unable to infect host cells.

The present invention also provides antibodies directed to the proteins of the present invention. The availability of antibodies to any given protein is highly advantageous, as it provides the basis for a wide variety of qualitative and quantitative analytical methods, separation and purification methods, and other useful applications directed to the subject proteins. Accordingly, given the present disclosure and the proteins of the present invention, it will be readily apparent to one skilled in the art that antibodies, in particular antibodies specifically binding to a protein of the present invention, can be prepared using well-established methodologies (e.g., such as the methodologies described in detail by Harlow et al. in Antibodies. A Laboratory Manual, Cold Spring Harbor Laboratory, Cold Spring Harbor, 1988, pp. 1-725). Such antibodies can comprise polyclonal or monoclonal antibodies, or fragments thereof. Furthermore, such antibodies can be obtained and employed either in solution-phase or coupled to a desired solid-phase matrix, such as magnetic beads or a flow through matrix. Having in hand such antibodies as provided by the present invention, one skilled in the art will further appreciate that such antibodies, in conjunction with well-established procedures (e.g., such as described by Harlow et al., 1988, supra) comprise useful methods for the detection, quantification, or purification of a polypeptide or conjugate of the invention, or host cell transformed to produce a polypeptide or conjugate of the invention. In one embodiment of the invention, a polypeptide or conjugate of the invention is attached to a sold support matrix by means of an antibody specific for a polypeptide of the invention or an effector molecule. Methods of achieving such attachment are well-known in the art (see, for example, Harlow et al. (1988) Antibodies: A Laboratory Manual, Cold Spring Harbor Laboratory, Cold Spring Harbor, N.Y.).

The present invention also provides a method for isolating (e.g., purifying) an oligosaccharide or polysaccharide comprising Man-alpha-(1→6)Man-beta (1→4) GlcNAc-beta (1→4)GlcNAc, comprising (a) contacting a sample suspected of comprising the oligosaccharide or polysaccharide with a polypeptide or conjugate of the invention, preferably wherein the polypeptide or conjugate is attached to a solid support matrix, under conditions effective for specific binding of the oligosaccharide or polysaccharide in the sample to the isolated polypeptide or conjugate in the composition; and (b) separating the sample and the composition, whereupon the oligosaccharide or polysaccharide is removed from other components of the sample. By "effective" conditions is meant conditions of salt, temperature, pH etc. which result in specific binding of the oligosaccharide to the polypeptide or conjugate and are effective for achieving the separation. Such conditions can be determined empirically, following routine procedures.

Another embodiment of the invention is a kit useful for any of the methods disclosed herein; such a kit comprises one or more isolated polypeptides and/or conjugates of the invention. For example, a kit suitable for therapeutic or prophylactic treatment of a virus infection (e.g., an HIV infection) in a subject may further comprise a pharmaceutically acceptable carrier and, optionally, a container or packaging material. In a kit suitable for removing a virus (e.g., HIV) from a sample, the isolated polypeptide(s) and/or conjugate(s) may be attached to a solid support matrix. Among other uses, kits of the invention can be used in experiments to study mechanisms by which MVL-like polypeptides bind to carbohydrates. A skilled worker will recognize components of kits suitable for carrying out any of the methods of the invention.

Optionally, the kits comprise instructions for performing the method. Kits of the invention may further comprise a support or matrix to which polypeptides or conjugates of the invention can be attached or immobilized. Other optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form for use as therapeutics, or in single reaction form for diagnostic use.

In the foregoing and in the following examples, all temperatures are set forth in uncorrected degrees Celsius; and, unless otherwise indicated, all parts and percentages are by weight.

EXAMPLES

I. Materials and Methods

A. Cells B-SC-1 cells (American Type Culture Collection) grown in Dulbecco-modified Eagle medium supplemented with 10% fetal bovine serum (DMEM 10%), 2 mM L-glutamine and 50 mg/mL gentamycin (all from Gibco BRL, Bethesda, Md.) were used for all assays.

B. Reagents Recombinant vaccinia viruses used in this study were obtained from the AIDS Research and Reference program, Division of AIDS, NIAID, National Institutes of Health, and include the following recombinants (donor in parentheses): vCB-32 encoding HIV-1 Env from SF162 (Broder et al. (1995) *Proc Natl Acad Sci USA* 92, 9004-9008), vCB-41 encoding HIV-1 Env from LAV (Broder et al. (1995) supra), vCBYF1-fusin encoding T-tropic receptor CXCR4 (Feng et al. (1996) *Science* 272, 872-877, vCB-CCR5 encoding M-tropic receptor CCR5 (gift from Dr. Christopher Broder) (Dimitrov et al. (1999) *Virology* 259, 1-6, vCB21R-LacZ encoding f-galactosidase (C. Broder, P. Kennedy, E. Berger), and vP11T7gene1 encoding T7 polymerase. Chlorophenol-red-$\beta$-D-galactopyranoside (CPRG) was purchased from Roche (Nutley, N.J.), and $^{15}$N—NH$_4$Cl was purchased from Cambridge Isotope Labs (Andover, Mass.). Mannobiose disaccharides were purchased from Sigma-Aldrich (St. Louis, Mo.), and GlcNAc$_2$, mannotriose, and all other high mannose complex carbohydrates were purchased from Glycotech (Rockville, Md.).

C. Expression and purification of uniformly labeled MVL Isolation and sequencing of the MVL gene from *M. viridis* NIES-102 strain has been described previously (Yamaguchi et al. (1999), supra). An insert spanning the MVL gene was generated by polymerase chain reaction using MVL pTV118N as template and purified primers 5'-cggtgcgag-catatggcgagttacaaagtg (SEQ ID NO: 5) and 5'-ggccacgctc-gagttagaaagtgtacttg (SEQ ID NO: 6) (Lofstrand Labs, Rockville, Md.), which encode NdeI and XhoI restriction sites, respectively. The MVL expression vector was constructed following digestion with NdeI and XhoI and cloning into pET11a expression vector (Novagen, Madison, Wis.) digested with the same endonucleases. The MVL insert was verified by DNA sequencing and expressed in *Escherichia coli* BL21 (DE3), and the composition confirmed by mass spectrometry.

Uniformly labeled $^{15}$N protein was obtained by growing cells at 37° C. in M1 minimal medium containing $^{15}$N—NH$_4$Cl and $^{12}$C-glucose as nitrogen and carbon sources, respectively. Upon reaching an optical density of ~1.0, cells were induced with 1 mM isopropyl-$\beta$-D-thiogalactoside for 3-4 hr and harvested by centrifugation at 7500×g for 10 min. Following resuspension and homogenization in 50 mM Tris, pH 8, 50 mM NaCl, 1 mM benzamidine at 4° C., cells were lysed in a microfluidizer, and a clear cell free extract was obtained after centrifugation at 16,000×g for 1 hr, 4° C. The supernatant was applied directly to a HiLoad™ 26/10 Q-Sepharose anion exchange column (Amersham Biosciences, Piscataway, N.J.) equilibrated in 20 mM Tris, pH 8 at a flow rate of 0.5 mL min$^{-1}$, and eluted with a linear gradient of 0 to 1 mM NaCl in 20 mM Tris, pH 8 over 10 column volumes. Fractions containing MVL were combined and concentrated in a 5000 MWCO filter and applied to a Superdex75 26/60 column equilibrated with 20 mM sodium phosphate (pH 6.5) and eluted with the same. Fractions containing pure MVL by SDS-PAGE on premade 20% Phast gels (Amersham Pharmacia Biotech) were combined and concentrated in a 5000 MWCO filter and stored at 4° C. until later use. Concentrations of all samples were determined spectrophotometrically based on the extinction coefficient calculated for a denatured monomer having the sequence shown in FIG. 1 ($\epsilon$26,600 M$^{-1}$ cm$^{-1}$ for monomer) (Gill et al. (1989) *Anal Biochem* 182, 319-326). Note that no measurable difference in absorbances was observed for identical samples diluted into 6 M guanidine HCl or phosphate buffer.

D. NMR Spectroscopy All NMR experiments were recorded at 27° C. on Bruker DMX500 and DMX600 spectrometers equipped with x,y,z-shielded gradient triple resonance probes or a z-shielded gradient triple resonance cryoprobe. Spectra were processed and peak volumes and heights measured using the software package NMRPipe (Delaglio et al. (1995) *J Bimol NMR* 6, 277-293). Titration experiments using 250 μL NMR samples of 0.15 mM $^{15}$N-MVL were performed by recording $^{1}$H-$^{15}$N heteronuclear single quantum coherence spectra of samples in the presence of varying stoichiometries of di-, tri-and oligosaccharides. Typically, 0.25 to 0.5 equivalents of ligand were added in 5 μL aliquots. All solutions were prepared in 20 mM sodium phosphate and the pH was adjusted to 6.85. $^{1}$H, $^{13}$C and $^{15}$N backbone assignments were made for free MVL and 1:2 MVL:Man$_3$ using 3D double and triple resonance through-bond correlation and NOE experiments including CBCA (CO)NH, CBCANH, HNCA and $^{15}$N separated NOE experiments (Clore et al. (1994) *Meth. Enzym.* 239, 349-363).

E. Isothermal Titration Calorimetry Measurements of oligo-mannose-MVL binding ITC measurements and analysis were performed with a Microcal VP-ITC titration calorimeter and Origin software. In each experiment 1.484 mL of 10 μM MVL were present in the solution cell, and 20-30 5 μL aliquots of ligand were added via a 250 μL rotating stirrer-syringe every 180 seconds at 25° C. The ligands included solutions of 800 μM Man$_2$A, Man$_3$ and Man$_6$, and 1.0 mM Man$\alpha$(1→2)Man$\alpha$(1→3)Man, Man$\alpha$(1→2)Man$\alpha$(1→6), mannotriose, GlcNAc$_2$, and an equimolar mixture of mannotriose:GlcNAc$_2$. All solutions were prepared in 10 mM Tris buffer, pH 6.5. Controls were performed for each experiment wherein the appropriate ligand solution was added to buffer only. In the case of all di-and tri-saccharide ligands, the binding isotherms were indistinguishable from those of the controls and could not be integrated indicating that no binding occurs to these carbohydrates.

F. Gel Filtration Gel filtration experiments were carried out on a Superdex75 10/30 column using an AKTA FPLC (both from Amersham Biosciences, Piscataway, N.J.). Samples of Dextran Blue (120 kDa), albumin (67 kDa), ovalbumin (43 kDa), chymotrypsinogen A(25 kDa), ΔQ50-cyanovirin-N(22 kDa) (Bewley et al. (1998) *Nature Struct. Biol.* 5, 571-578), ribonuclease A (13.7 kDa), cyanovirin-N (11 kDa) and aprotinin (6.7 kDa) were used to calibrate the column eluting with a flow rate of 0.8 mL/min in PBS 7.0.

G. Sedimentation Equilibrium Sedimentation equilibrium experiments were conducted at 25.0° C. and three different rotor speeds (12,000, 14,000 and 16,000) on a Beckman Optima XL-A analytical ultracentrifuge. Protein samples were prepared in 20 mM sodium phosphate buffer (pH=6.85) and loaded into the ultracentrifuge cells at nominal loading concentrations of 0.8 $A_{280}$. Data were analyzed in terms of a single ideal solute to obtain the buoyant molecular mass, $M(1-\upsilon\rho)$, using Sigma Plot 2002 (SPPS Inc.) The value for the experimental molecular mass M was determined using calculated values for the density $\rho$ (determined at 25.0° C. using standard tables) and partial specific volume $\upsilon$ (calculated on the basis of amino acid composition (S. J. Perkins (1986) *Eur. J. Biochem.* 15, 169-180).

H. Cell Fusion Assays HIV-1 Env-mediated cell fusion assays on MVL were carried out as described previously (Louis et al. (2003) *J. Biol. Chem.* 278, 20278-20285). B-SC-1 cells were used for both target and effector cell populations. For experiments employing T-cell-tropic Env, target cells were co-infected with recombinant vaccinia viruses vCB21R-LacZ and vCBYF1-fusin, and effector cells with vCB41 and vP11T7gene1, at an MOI of 2.5. In the experiments employing macrophage-tropic Env, target cells were co-infected with vCB-CCR5 and vCB21R-LacZ, and target cells with vCB21 and vP11T7gene 1. Following infection, cells were incubated for 18 h at 32° C. to allow for vaccinia virus-mediated expression of recombinant proteins. For inhibition studies, proteins or complexes were added to an appropriate volume of DMEM 2.5% and PBS to yield identical buffer compositions (100 μL), followed by addition of 1×10$^5$ effector cells (in 50 μL media) per well and 1×10$^5$ target cells (in 50 μL media) per well. Soluble CD4 was added to the media of the target cells at a concentration of 800 nM to yield a final concentration of 200 nM soluble CD4 per well. Following 2.5 hr incubation at 37° C., β-galactosidase activity of cell lysates was measured from the absorbance at 570 nm (Molecular Devices 96-well spectrophotometer) upon addition of CPRG. The curves for % fusion versus MVL concentration were fit by non-linear least-squares optimization using the program Kaleidagraph 3.5 (Synergy Software, Reading, Pa.).

II. Determining Carbohydrate Specificity by NMR

To determine carbohydrate specificity for MVL in detail, we carried out a series of NMR titration studies by recording $^1$H-$^{15}$N correlation spectra on samples of uniformly labeled 15N-MVL in the presence of increasing amounts of the various mannose-containing carbohydrates illustrated in FIG. 1. Many of these carbohydrates are shown in FIG. 1. These included α-linked mannobioses Manα(1→2)Manα, Manα(1→3)Manα, Manα(1→4)Manα, and Manα(1→6)Manα; their β-linked counterparts (structures not shown); the disaccharide Manβ(1→4)GlcNAc; the tetrasaccharide Man$_2$A (Manα(1→6)Manβ(1→4)GlcNAcβ(1→4)GlcNAc); and high mannose oligosaccharides Man$_3$GlcNAc$_2$, Man$_5$GlcNAc$_2$, Man$_6$GlcNAc$_2$ and Man$_9$GlcNAc$_2$. Spectra of MVL in the presence of stoichiometric excesses of each of the above mentioned disaccharides were identical to that of free MVL (spectra not shown), indicating that MVL does not bind to any of these molecules. In contrast, addition of oligomannose structures such as Man$_3$GlcNAc$_2$ and Man$_6$GlcNAc$_2$ causes dramatic changes in the $^1$H-$^{15}$N correlation spectra. As seen in FIGS. 2A and 2B, nearly one third of the backbone and side chain amide resonances undergo large changes in chemical shift upon binding to these complex carbohydrates. Similarly, substantial changes in the $^1$H-$^{15}$N correlation spectra of MVL were also observed upon addition of each of the high mannose oligosaccharides listed in Table 1. Direct comparisons of the $^1$H-$^{15}$N correlation spectra of MVL in the presence of excess amounts of the various oligomannoses revealed that MVL binds each of these carbohydrates in a slightly different manner as none of the spectra are identical. For example, superposition of the $^1$H-$^{15}$N correlation spectra for 1:4 complexes of MVL:Man$_3$GlcNAc$_2$ and MVL:Man$_6$GlcNAc$_2$ shows that roughly eight backbone and/or side chain amides resonate at different chemical shifts in the two complexes (FIG. 2C). Moreover, a direct comparison of all possible combinations of MVL:oligomannose complexes (overlaid spectra not shown) indicated that the more complex the carbohydrate ligand, the greater the number of resonances observed to change upon binding.

Each of the oligomannose structures shown to bind to MVL contains at least one of the conserved disaccharide or trisaccharide core structures Manβ(1→4)GlcNAc, GlcNAcβ(1→4)GlcNAc, GlcNAc$_2$) and Manα(1→3)[Manα(1→6)]Manβ(mannotriose). To determine whether MVL recognizes these smaller substructures, we carried out titration studies with other compounds, including GlcNAc$_2$ and Mannotriose. NMR spectra for MVL in the presence of even a 10-fold excess of any of these carbohydrates were identical to that of free MVL where neither perturbation of chemical shifts nor changes in cross peak intensity or line width were detected. To simulate the larger oligomannose core structures, such as Man$_2$A and Man$_3$GlcNAc$_2$, we also titrated in 1:1 mixtures of Manα(1→6)Manα:GlcNAc$_2$, Manα(1→3)Manα:GlcNAc$_2$, and Manα(1→3)[Manα(1→6)]Manβ: GlcNAc$_2$. Again, NMR spectra were identical for free MVL versus MVL in the presence of excesses of each of these mixtures. These results indicate that in terms of natural oligosaccharides present in mammalian systems, the smallest structure MVL binds with high affinity is Man$_2$A. (It remains possible that MVL would bind the truncated trisaccharide Manα(1→6)Manβ(1→4)GlcNAc with similar affinity, but this carbohydrate was not available for binding studies.)

TABLE 1

| Mannose-containing carbohydrates used for MVL binding studies. | |
|---|---|
| Carbohydrate | Binding to MVL |
| GlcNAcβ(1→4) GlcNAc | — |
| Manα(1→2)Man | — |
| Manα(1→3)Man | — |
| Manα(1→4)Man | — |
| Manα(1→6)Man | — |
| Manβ(1→2)Man | — |
| Manβ(1→3)Man | — |
| Manβ(1→4)Man | — |
| Manβ(1→6)Man | — |
| Manβ(1→4)GlcNAc | — |
| Manα(1→2)Manα(1→2)Man | — |
| Manα(1→2)Manα(1→3)Man | — |
| Manα(1→2)Manα(1→6)Man | — |
| Manα(1→3)[Manα(1→6)]Man | — |
| 1:1 Manα(1→3)Man:GlcNAc$_2$ | — |
| 1:1 Manα(1→6)Man:GlcNAc$_2$ | — |
| 1:1 Manα(1→3)[Manα(1→6)]Man:GlcNAc$_2$ | — |

TABLE 1-continued

Mannose-containing carbohydrates used for MVL binding studies.

| Carbohydrate | Binding to MVL |
|---|---|
| oligomannose-2A | 3 |
| oligomannose-3 | 3 |
| oligomannose-5 | 3 |
| oligomannose-6 | 3 |
| oligomannose-9 | 3 |

III. MVL Binds Oligomannosides Through Two Binding Sites in Slow Exchange

The concentrations of the NMR samples of MVL were determined spectrophotometrically from the extinction coefficient calculated for a denatured monomer having the sequence shown within FIG. 3 ($\epsilon$26 600 M$^{-1}$ cm$^{-1}$). Spectral expansions of the $^1$H-$^{15}$N correlation spectra were recorded at individual points during the titration of Man$_3$GlcNAc$_2$ to MVL. As can be seen in the expansions in FIG. 3C taken from the upfield region of the $^1$H,$^{15}$N correlation spectra where cross peaks for Gly 10 and Gly 69 appear, addition of 0.5 equivalents of Man$_3$, based on the concentrations calculated for monomer, resulted in the appearance of several new cross peaks whose average volume integrates to approximately one fourth that of resonances corresponding to free MVL; and addition of a second 0.5 equivalent gives rise to cross peaks with approximately one half the intensity of free resonances. Similar changes in cross peak intensities were observed during the course of the titration until a two-fold excess of carbohydrate had been added, at which time no further changes in appearance or disappearance of cross-peaks were observed, nor were any changes in volume observed. In terms of stoichiometry, similar changes in the intensities of cross peaks for the carbohydrate-bound state of MVL also were observed in the $^1$H-$^{15}$N correlation spectra for individual points of the titrations of oligomannose-6 and oligomannose-9 to $^{15}$N-MVL. Collectively, these results demonstrate that two carbohydrate binding sites are present in each MVL monomer, and that MVL binds oligomannose structures with sufficiently high affinity to be in slow exchange on the NMR time scale (see below).

IV. Identification of Carbohydrate Binding Sites

In preparation for solving the three-dimensional solution structure of MVL in complex with a representative oligomannose structure, Man$_3$, we completed backbone resonance assignments (including HN, N, H$\alpha$, C$\alpha$, H$\beta$ and C$\beta$ atoms) for both free MVL and a 1:2 MVL:Man$_3$ complex using multi-dimensional NMR techniques. With these resonance assignments in hand, the difference in backbone HN and N chemical shifts for free and bound MVL were directly compared and plotted as a function of residue number (FIG. 3). The presence of two homologous carbohydrate binding sites is readily apparent from the plot which shows similar patterns of $\Delta\delta_{SUM}$ values present in the two tandemly repeated domains (where $\Delta\delta_{SUM}=\sqrt{(\Delta\delta_{HN}^2+\Delta\delta_N^2)}$). Sequences displaying average $\Delta\delta_{SUM}$ values greater than ~50 Hz are observed in four regions of the protein, with each region comprising approximately 15 amino acids. These include regions encompassing residues 10-25, 36-49, 67-83 and 95-108, all of which include one tryptophan residue. Comparison of the sequence alignments and the $\Delta\delta_{SUM}$ values of the two tandem repeats thus indicate that the two carbohydrate binding regions are composed of the conserved sequences GPLWSNXEAQXXGPX (SEQ ID NO: 1, corresponding to residues 10-24 and 69-83) and FTGQWXTXVEXXMSV (SEQ ID NO: 2, corresponding to residues 33-47 and 92-106). Backbone chemical shift assignments also revealed that $\Delta\delta$ values range from less than 10 Hz to greater than 800 Hz for HN atoms. Thus, the lifetime of the MVL:Man$_6$ complex is $\gg$16 ms [$(2\pi\Delta\delta)^{-1}$]. The observation that a single set of resonances appeared during the course of each of the titrations indicated that the two carbohydrate binding sites bind these various oligomannosides with comparable affinities under the conditions used for the NMR titrations (micromolar concentrations at pH 6.85).

V. Isothermal Titration Calorimetry

To determine the equilibrium association constants and thermodynamic parameters for MVL binding to representative oligomannosides, isothermal titration calorimetry measurements were performed for several of the carbohydrates shown to bind to MVL by NMR. As seen in the representative equilibrium titration curves for MVL binding to Man$_3$GlcNAc$_2$ and Man$_6$GlcNAc$_2$ (FIGS. 4A and 4B, respectively), each of these oligosaccharides bind MVL with large negative enthalpies (Table 2) indicating that MVL—carbohydrate interactions are dominated by electrostatic interactions. Calculations of the free energies of binding show that each of the three oligosaccharides also binds MVL with favorable free energies ranging from −7.4 to −9.0 kcal mol$^{-1}$ (Table 2). However, as one would expect, steady increases in entropic cost are observed for binding to MVL as the carbohydrate ligands become larger and more complex with values ranging from −10.7 cal mol$^{-1}$ for Man$_2$A to −39.5 cal mol$^{-1}$ for Man$_6$. Curve fitting of the binding isotherms using a one independent site model for Man$_2$GlcNAc$_2$, Man$_3$GlcNAc$_2$ and Man$_6$GlcNAc$_2$ yielded a stoichiometry of binding equal to two carbohydrates per monomer for each of these ligands (Table 2). Curve fitting was also attempted using a two independent site model and a two sequential binding site model. However, fits to both models resulted in error values at least one order of magnitude greater than that generated by the one independent site model. When considered together with the results of the NMR titration experiments wherein the positions of a large number of cross peaks changed concurrently upon carbohydrate binding and a stoichiometry of 2:1 carbohydrate:MVL was observed, these measurements indicate that in terms of affinity, the two carbohydrate recognition domains present in MVL are nearly equivalent, thereby binding these ligands in a similar manner. These results are supported by the symmetry observed for the $\Delta\delta$ values illustrated in FIG. 2.

TABLE 2

Isothermal titration calorimetry data.

| Carbohydrate | Stoichiometry | $K_a$ M$^{-1}$ | $\Delta$H kcal mol$^{-1}$ | $\Delta G^a$ kcal mol$^{-1}$ | $\Delta$S cal mol$^{-1}$ |
|---|---|---|---|---|---|
| Man$_2$A | 2.04 ± 0.05 | 2.4 (±0.2) × 10$^5$ M$^{-1}$ | −10.5 ± 0.04 | −7.4 ± 0.6 | −10.7 ± 2.1 |
| Man$_3$ | 2.15 ± 0.02 | 3.5 (±0.2) × 10$^5$ M$^{-1}$ | −13.1 ± 0.1 | −7.5 ± 0.4 | −18.7 ± 5.1 |
| Man$_6$ | 2.06 ± 0.01 | 4.5 (±0.3) × 10$^6$ M$^{-1}$ | −20.8 ± 0.1 | −9.0 ± 0.6 | −39.5 ± 2.3 |

$^a\Delta G = -RT \cdot \ln K_A$;
T = 298 K

VI. Oligomeric Nature of MVL-MVL is a Monodisperse Dimer

As many carbohydrate binding proteins exhibit oligomeric structures, we sought to examine the oligomeric state of MVL using biophysical techniques. Thus, a sample of MVL was analyzed by gel filtration chromatography using a Superdex75 column calibrated as described earlier (Yang et al. (1999) *J. Mol. Biol.* 288, 403-412). Elution profiles clearly indicated that MVL was considerably larger than a monomer, and extrapolation from the linear plot of log molecular weight as a function of elution volume (FIG. 5A) showed the protein to have a molecular mass of 25.4 kDa. Sedimentation equilibrium experiments were subsequently carried out on a sample of MVL at three different rotor speeds. In all cases, sedimentation equilibrium data were best modeled in terms of a single ideal solute (FIG. 5B) yielding identical values of the buoyant molecular mass and indicating that the sample was monodisperse. A global analysis yields a value of 6,170±100 g mol$^{-1}$ for M(1-vρ) which corresponds to a measured molecular mass of 23,340±400 g mol$^{-1}$, and indicates that under these conditions MVL is dimeric ($M_{calc}$=12,237.4 g mol$^{-1}$, n=1.9±0.03). Together, these results firmly establish that MVL is a dimer in solution. Moreover, on the basis of the NMR data, the three-dimensional structure of MVL must be a symmetric dimer because a single set of resonances (corresponding to the number expected from the amino acid sequence) are observed in the $^1$H-$^{15}$N correlation spectra of both free and fully bound MVL.

Additional sedimentation equilibrium measurements were made on three separate samples of 30 □M MVL containing a four-fold molar excess of either oligomannose-3, oligomannose-6 or oligomannose-9. As MVL binds Man$_3$ and Man$_6$ with apparent equilibrium constants of 3.5 (±0.2)×10$^5$ M$^{-1}$ and 4.5 (±0.3)×10$^6$ M$^{-1}$, respectively (Table 2), the MVL dimer is expected to be saturated with the oligosaccharide. In all cases, data were best fit in terms of a single ideal solute yielding experimental molecular masses corresponding with a monodisperse MVL dimer bound to at least 4 (average n=5.4±1.1) oligomannose moieties (data not shown). Although the resolution and error of the sedimentation method does not allow us to distinguish between 4, 5, or 6 oligomannose species bound to an MVL dimer, the data appear to be consistent with the stoichiometry determined by isothermal titration calorimetry. Thus, at micromolar concentrations, these branched ligands do not appear to induce cross-linking of MVL. Moreover, these results are entirely consistent with specific recognition of the tetra-or pentasaccharides Man$_2$A and Man$_3$, structures located in the internal core (FIG. 2) as opposed to the terminal branching arms of high mannose structures. This mode of binding is illustrated schematically in FIG. 5C where multi-domain carbohydrate binding proteins that recognize terminal structures can be cross-linked by the branching, providing the spacing separating binding sites is greater than that separating terminal saccharide units; and those recognizing internal core structures, or non-branching oligosaccharides are simply saturated with the ligand.

VII. MVL Inhibits HIV-1 Envelope Mediated Fusion

There are several reports of lectins exhibiting antiviral activity toward HIV. Complex and especially high mannose type oligosaccharides account for nearly half of the molecular mass of gp120, and these antiviral lectins likely bind to oligosaccharides displayed over much of the envelope surface, thereby interfering with the fusion event. The magnitude of antiviral activity for various carbohydrate binding proteins correlates with the types of oligosaccharide present on the viral surface (Hansen et al. (1991) *Scand. J. Infect. Dis.* 23, 425-430; Balzarini et al. (1992) *Antiviral. Res.* 18, 191-207).

Given the high affinities with which MVL can bind various high mannose oligosaccharides, we evaluated its effect on HIV-1 Env-mediated fusion in a quantitative vaccinia virus reporter gene assay that faithfully reproduces the events that lead to membrane fusion (Salzwedel et al. (2000) *J. Virol* 74, 326-333). MVL was tested for its ability to inhibit an HIV-1 T-cell tropic (T-tropic) strain LAV, and a macrophage tropic (M-tropic) strain SF162, with inhibition curves for both virus types shown in FIG. 6A. Titration data were best fit to a two-independent site model comprising two molecules of MVL per molecule of gp120, as fitting to a one-independent site model gave systematic errors in the fit. Best fits of the inhibition curves for LAV and SF162 viruses yield respective IC$_{50}$ values of 30±4 and 37±6 nM (given by ($\sqrt{2}$−1)/K$_A$.

In a single round HIV-infectivity assay using the M-tropic virus SF162 and a T-tropic virus (LAV) we have shown that MVL blocks HIV infectivity and have measured approximate IC50 values of 30-50 nM for these host cell types.

Competition experiments with several oligosaccharides against MVL were also carried out. Pretreatment of MVL with oligomannose-3 and oligomannose-9 resulted in partially reduced inhibition of fusion by MVL (FIG. 6B), and pretreatment with mannotriose had no effect as expected from NMR and ITC results. However, pre-treatment of MVL with one equivalent of gp120 (SF162) resulted in blocking MVL's inhibitory action by nearly 90%. Together, these results support the notion that MVL inhibits fusion through carbohydrate-mediated interactions with high mannose residues on gp120. The observation that preincubation with excess carbohydrate did not fully block MVL's activity while pretreatment with one equivalent of gp120 did suggests that MVL binds gp120 through multivalent interactions whose avidity surpasses that of MVL binding to individual oligomannosides.

VIII. The MVL Polypeptide Inhibits Viral Infection In Vivo (in a Primate Model)

An MVL polypeptide is tested for its ability to prevent rectal transmission of the SIV/HIV virus SHIV89.6P in macaques, when administered as a topical microbicide. Experiments are carried out essentially as described in Tsai et al. (2003) *AIDS Res. Hum. Retroviruses* 19, 535-541. Briefly, a gel-formulated recombinant MVL preparation is used as a topical microbicide in male macaques that are rectally challenged with the mentioned virus. All of the untreated macaques are infected and experience CD4$^+$ T cell depletion. By contrast, none of the macaques that receive either 1% or 2% MVL gel show evidence of SHIV89.6P infection. Furthermore, neither MVL not placebo gels produce adverse effects in any macaque following the rectal application.

IX. Fragments, Variants and Various Forms of MVL Inhibit HIV-1 Envelope Mediated Fusion Expression vectors are generated by conventional methods, such that, instead of full-length MVL, the peptide sequences represented by SEQ ID NO: 1 or SEQ NO:2 are expressed. In other constructs, the expressed polypeptide comprises (or consists of) SEQ ID NO: 1 and SEQ ID NO: 2, separated by a spacer of nine amino acids. Fragments or variants of these polypeptides, as discussed above (e.g., polypeptides comprising conservative substitutions, etc.), are also produced. The polypeptides are generally in the form of a dimer; in some cases, they are in the form of a higher multimer, or a monomer.

For each polypeptide, NMR studies are performed to determine whether the polypeptide is properly folded. Then the polypeptides are tested in an HIV-1 Envelope-mediated fusion assay. Methods for performing all of these studies are well-known in the art; some such studies are described elsewhere herein.

In addition, NMR titration studies are performed as described above with each of the polypeptides, using various oligomannoses. In some experiments, only one sugar is used.

The experiments are expected to identify those polypeptides which bind specifically to oligomannoses, such as $Man_2$-A or Man3, and which inhibit HIV-1 Envelope mediated fusion.

X. Further Characterization of the Structure of MVL

The 3-dimensional structures of MVL was determined by both multi-dimensional heteronuclear NMR and X-ray crystallography. These data showed the protein to exist exclusively as a homodimer. The homodimer comprises four homologous domains contributed by two units each corresponding to the N-and C-terminal domains. In terms of topology, the N-and C-terminal domains contain a triple-stranded beta sheet atop which lies one alpha helix. The N-and C-terminal domains are connected by a five amino acid linker (underlined in the sequence in FIG. 2) that is in an extended conformation. These features lead to the overall globular shape of each monomer of MVL appearing as a thick V or horse shoe. In the homodimeric structure shown in FIG. 7, the two V's appear to interlock where the monomers are positioned orthogonal to one another. The carbohydrate binding sites that were mapped by NMR titration experiments can be clearly delineated and comprise a binding pocket that surrounds the reducing N-acetyl glucosamine ring and a groove in which the remainder of the carbohydrate lies (shown by arrows in FIG. 7C).

The 3-dimensional structure of a complex of 1:2 MVL:oligomannose-3 is consistent with the chemical shift mapping shown in FIG. 2 and suggests that the following residues are key to carbohydrate recognition and binding: In domain one (or the N-terminal domain), Trp 13, Ser 14, Asn 15, Glu 17, Ala 18, Gln 19, Gln 20, Lys 24, Gln 36, Trp 37, Thr 38, Thr 39, Val 40, Glu 42, Ser 43, Ala 44 and Ser 46. Key amino acids in domain two (or the C-terminal domain) include Trp 72, Ser 73, Asn 74, Asp 75, Glu 76, Ala 77, Gln 78, Lys 79, Gln 83, Gln 95, Trp 96, Arg 97, Thr 98, Glu 101, Gly 102, Val 103, Ser 105. In addition, proline residues 11 and 70 appear to contribute not only to carbohydrate binding but to changes in the backbone conformation which help to form the binding site. It is expected that conserved amino acids can be substituted in place of these key amino acids. For example, Asp replaced by Glu, or Arg replaced by Lys, etc. would be expected to have minimal effects on recognition and binding.

Smaller peptides (fragments) whose sequences comprise the binding sites and explicitly, the amino acids listed above, may have some carbohydrate binding affinity outside of the context of the complete protein.

Other methods relevant to the invention are described in U.S. Pat. Nos. 6,586,392; 6,428,790; 6,420,336; 6,245,737; 6,193,982; 6,015,876; 5,998,587; 5,962,668; 5,962,653; 5,843,882; 5,821,081; US patent publications: 20030166552; 20030103997; 20020151476; 20020127675; 20020110557.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, including U.S. provisional application U.S. provisional application 60/551,058, filed Mar. 9, 2004, cited above and in the figures are hereby incorporated by reference.

I claim:

1. An isolated polypeptide, which comprises two sequences, chosen from the group consisting of:
   a) the amino acid sequence GPLWSNXEAQXXGPX (SEQ ID NO: 1) separated by about 6-15 amino acids from the amino acid sequence FTGQWXTXVEXXMSV (SEQ ID NO: 2);
   b) SEQ ID NO: 1 separated by about 6-15 amino acids from an active variant of SEQ ID NO: 2;
   c) an active variant of SEQ ID NO:1 separated by about 6-15 amino from SEQ ID NO: 2,
   wherein the polypeptide binds specifically to an oligosaccharide comprising the tetrasaccharide Man-alpha-(1→6)Man-beta (1→4) GlcNAc-beta(1→4)GlcNAc,
   provided that the polypeptide does not comprise SEQ ID NO: 3.

2. An isolated polypeptide, wherein the polypeptide binds specifically to an oligosaccharide comprising the tetrasaccharide Man-alpha-(1→6)Man-beta (1→4) GlcNAc-beta(1→4) GlcNAc, provided that the polypeptide does not comprise SEQ ID NO: 3,
   wherein the polypeptide comprises two copies of the sequence GPLWSNXEAQXXGPX (SEQ ID NO: 1), located approximately at positions 10-24 and 69-83 of the polypeptide, and two copies of the sequence FTGQWXTXVEXXMSV (SEQ ID NO: 2), located approximately at positions 33-47 and 92-106 of the polypeptide.

3. The polypeptide of claim 1, wherein the polypeptide is in the form of a homodimer.

4. The polypeptide of claim 1, wherein the polypeptide has antiviral activity.

5. The polypeptide of claim 4, which inhibits fusion of an enveloped virus comprising a glycoprotein comprising the tetrasaccharide Man-alpha-(1→6)Man-beta (1→4) GlcNAc-beta(1→4)GlcNAc to a target cell.

6. The polypeptide of claim 4, which has anti-HIV activity.

7. A pharmaceutical composition, comprising an antiviral effective amount of a polypeptide selected from the group consisting of:
   a) a first isolated polypeptide comprising two sequences selected from the group consisting of:
      i) the amino acid sequence GPLWSNXEAQXXGPX (SEQ ID NO: 1) separated by about 6-15 amino acids from the amino acid sequence FTGQWXTXVEXXMSV (SEQ ID NO: 2);
      ii) SEQ ID NO: 1 separated by about 6-15 amino acids from an active variant of SEQ ID NO: 2;
      iii) an active variant of SEQ ID NO:1 separated by about 6-15 amino acids from SEQ ID NO:2; and
   b) a second isolated polypeptide comprising two copies of the amino acid sequence GPLWSNXEAQXXGPX (SEQ ID NO: 1), located approximately at positions 10-24 and 69-83 of the second isolated polypeptide, and two copies of the sequence FTGQWXTXVEXXMSV (SEQ ID NO: 2), located approximately at positions 33-47 and 92-106 of the second isolated polypeptide;
   and a pharmaceutically acceptable carrier; provided that the polypeptide does not comprise SEQ ID NO:3.

8. The pharmaceutical composition of claim 7, which is formulated for topical administration.

9. An isolated polypeptide, which comprises two copies of the amino acid sequence GPLWSNXEAQXXGPX (SEQ ID NO: 1) separated by about 6-15 amino acids from the amino acid sequence FTGQWXTXVEXXMSV (SEQ ID NO: 2), wherein the polypeptide binds specifically to an oligosaccharide comprising the tetrasaccharide Man-alpha-(1→6)Man-beta (1→4) GlcNAc-beta(1→4)GlcNAc, provided that the polypeptide does not comprise SEQ ID NO: 3.

10. The polypeptide of claim 2, wherein the polypeptide is in the form of a homodimer.

11. The polypeptide of claim 9, wherein the polypeptide is in the form of a homodimer.

12. The polypeptide of claim 2, wherein the polypeptide has antiviral activity.

13. The polypeptide of claim 9, wherein the polypeptide has antiviral activity.

14. The polypeptide of claim 12, which inhibits fusion of an enveloped virus comprising a glycoprotein comprising the tetrasaccharide Man-alpha-(1→6)Man-beta (1→4) GlcNAc-beta(1→4)GlcNAc to a target cell.

15. The polypeptide of claim 13, which inhibits fusion of an enveloped virus comprising a glycoprotein comprising the tetrasaccharide Man-alpha-(1→6)Man-beta (1→4) GlcNAc-beta(1→4)GlcNAc to a target cell.

16. The polypeptide of claim 12, which has anti-HIV activity.

17. The polypeptide of claim 13, which has anti-HIV activity.

18. A composition comprising one or more isolated polypeptides of claim 1, 2, or 9, wherein the polypeptides are attached to a support.

19. A conjugate of an isolated polypeptide of claim 1, 2, or 9, and an effector molecule.

20. A method for removing a virus from a sample, comprising
   a) contacting a sample suspected of containing the virus with an antiviral effective amount of a composition comprising
      (i) an isolated polypeptide of claim 1, 2, or 9; or
      (ii) a conjugate of an isolated polypeptide of claim 1, 2, or 9 and an effector molecule, under conditions effective for binding of the virus in the sample to the isolated polypeptide and/or conjugate; and
   b) separating the sample and the composition, whereupon virus is removed from the sample.

21. The method of claim 20, wherein the isolated polypeptide or conjugate is attached to a solid support matrix.

22. The method of claim 20, wherein the sample is an inanimate object.

23. The method of claim 20, wherein the sample is a bodily fluid.

24. A complex comprising
an isolated polypeptide of claim 1, 2, or 9, or a conjugate thereof;
and a viral envelope glycoprotein.

25. A kit suitable for therapeutic or prophylactic treatment of a virus infection in a subject, comprising
an isolated polypeptide of claim 1, 2, or 9, wherein the polypeptide binds specifically to an oligosaccharide comprising the tetrasaccharide Man-alpha-(1→6)Man-beta (1→4) GlcNAc-beta(1→4)GlcNAc;
a pharmaceutically acceptable carrier; and
a container for the polypeptide.

26. A kit suitable for removing a virus from a sample, comprising a polypeptide or conjugate selected from the group consisting of:
a first isolated polypeptide, wherein the first isolated polypeptide is an isolated polypeptide of claim 1, 2, or 9;
a second isolated polypeptide, wherein the second isolated polypeptide exhibits at least about 90% sequence identity to an isolated polypeptide of claim 1, 2, or 9; and
a conjugate of the first or second isolated polypeptide and an effector molecule;
wherein the polypeptide or the conjugate is covalently attached to a solid support matrix, and wherein it is provided that the polypeptide or the conjugate does not comprise SEQ ID NO: 3.

* * * * *